US00RE43878E

(19) United States
(12) Reissued Patent
Li et al.

(10) Patent Number: US RE43,878 E
(45) Date of Reissued Patent: Dec. 25, 2012

(54) AMIDOPHENOXYINDAZOLES USEFUL AS INHIBITORS OF C-MET

(75) Inventors: Tiechao Li, Indianapolis, IN (US); Mark Andrew Pobanz, Indianapolis, IN (US); Chuan Shih, Indianapolis, IN (US); Zhipei Wu, Indianapolis, IN (US); Wei Jennifer Yang, Indianapolis, IN (US); Boyu Zhong, Indianapolis, IN (US)

(73) Assignee: Eli Lilly and Company, Indianapolis, IN (US)

(21) Appl. No.: 13/374,053

(22) Filed: Dec. 8, 2011

Related U.S. Patent Documents

Reissue of:
(64) Patent No.: 8,030,302
Issued: Oct. 4, 2011
Appl. No.: 12/503,223
Filed: Jul. 15, 2009

U.S. Applications:
(60) Provisional application No. 61/083,294, filed on Jul. 24, 2008, provisional application No. 61/085,082, filed on Jul. 31, 2008, provisional application No. 61/108,659, filed on Oct. 27, 2008.

(51) Int. Cl.

| | |
|---|---|
| ***A61K 31/416*** | (2006.01) |
| ***A61K 31/4439*** | (2006.01) |
| ***A61K 31/444*** | (2006.01) |
| ***A61K 31/501*** | (2006.01) |
| ***C07D 401/14*** | (2006.01) |
| ***C07D 413/14*** | (2006.01) |
| ***C07D 403/12*** | (2006.01) |

(52) U.S. Cl. ..... 514/232.5; 514/234.5
(58) Field of Classification Search ..... None
See application file for complete search history.

(56) References Cited

U.S. PATENT DOCUMENTS

| | | | |
|---|---|---|---|
| 6,608,049 | B2 | 8/2003 | Woltering et al. |
| 7,737,153 | B2 | 6/2010 | Feurer et al. |
| 2005/0288290 | A1 | 12/2005 | Borzilleri et al. |
| 2006/0004006 | A1 | 1/2006 | Borzilleri et al. |
| 2006/0211695 | A1 | 9/2006 | Borzilleri et al. |

FOREIGN PATENT DOCUMENTS

| | | |
|---|---|---|
| WO | 2006/116713 | 11/2006 |
| WO | WO 2007/075567 | 5/2007 |
| WO | 2007/103308 | 9/2007 |
| WO | WO 2008/008539 | 1/2008 |
| WO | WO 2008/051808 | 5/2008 |
| WO | 2009/003084 | 3/2009 |

*Primary Examiner* — Kamal Saeed
(74) *Attorney, Agent, or Firm* — Tina M. Tucker

(57) ABSTRACT

The present invention provides amidophenoxyindazole compounds useful in the treatment of cancer.

15 Claims, No Drawings

AMIDOPHENOXYINDAZOLES USEFUL AS INHIBITORS OF C-MET

Matter enclosed in heavy brackets [ ] appears in the original patent but forms no part of this reissue specification; matter printed in italics indicates the additions made by reissue.

*This application claims the priority of U.S. provisional patent application 61/083,294 filed Jul. 24,2008, U.S. provisional patent application 61/085,082 filed Jul. 31, 2008, and U.S. provisional patent application 61/108,659 filed Oct. 27, 2008.* c-Met is a member of the tyrosine kinase growth factor receptor family. c-Met expression occurs in endothelial, epithelial, and mesenchymal cells. Binding to c-Met of the endogenous ligand, hepatocyte growth factor (HGF), promotes cell migration, proliferation, and invasion.

c-Met is implicated in the progression of certain tumors. c-Met overexpression has been shown in numerous tumor types including colon, breast, renal, lung, hemangiomas, squamous cell myeloid leukemia, melanomas, glioblastomas, and astrocytomas. Activation of tumor cell c-Met receptors enhances tumor cell proliferation, invasion/metastasis, and resistance to apoptosis and cytotoxic therapies.

Various amidophenoxyheteroaryl c-Met inhibitors have been reported. See for example, US2005/0288290, US2006/0211695, US2006/0004006, and WO 2007103308.

However, there is still a need for further compounds that inhibit c-Met. The present invention provides novel amidophenoxyindazole compounds believed to have clinical use for treatment of cancer through inhibiting c-Met. Preferred compounds of the present invention are also believed to provide an improvement in potency over certain other c-Met inhibitor compounds found in the art.

The present invention provides compounds of Formula I:

A compound of the formula:

Formula I

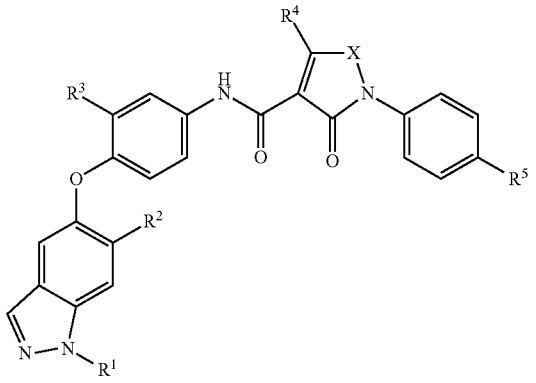

wherein:

$R^1$ is H or methyl;

$R^2$ is amino, dimethylamino, fluoro, cyclopropyl, pyridyl optionally substituted with an amino substituent or 1-2 methyl substituents, pyrazolyl optionally substituted with two methyl substituents, 2-methoxy-pyrimidin-5-yl, 4-methylsulfonylphenyl, tetrahydro-2H-pyran-4-ylamino, (tetrahydro-2H-pyran-4-yl)amino carbonyl, or a morpholin-4-yl substituent:

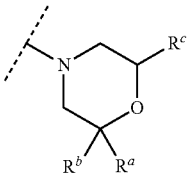

where $R^a$, $R^b$ and $R^c$ are independently selected from H or methyl;

$R^3$ is H or F;

$R^4$ is H, methyl, piperidin-1-ylmethyl, morpholin-4-ylmethyl, or pyrazol-1-ylmethyl;

$R^5$is H or F; and

X is CH═N, CH═CH, CH═C($CH_3$), C($CH_3$)═CH, C($CH_3$)═N, N($CH_3$), or [C(morpholin-4ylmethyl)═CH] *C(morpholin-4-ylmethyl)═CH*;

or a pharmaceutically acceptable salt thereof.

The present invention provides a method of treating cancer selected from the group consisting of lung cancer, breast cancer, colorectal cancer, renal cancer, pancreatic cancer, head cancer, neck cancer, hereditary papillary renal cell carcinoma, childhood hepatocellular carcinoma, and gastric cancer in a mammal comprising administering to a mammal in need of such treatment an effective amount of a compound of Formula I or a pharmaceutically acceptable salt thereof.

The present invention also provides a pharmaceutical composition comprising a compound of Formula I or a pharmaceutically acceptable salt thereof, and a pharmaceutically acceptable carrier, diluent or excipient.

This invention also provides a compound of Formula I or a pharmaceutically acceptable salt thereof for use as a medicament. Additionally, this invention provides use of a compound of Formula I or a pharmaceutically acceptable salt thereof in the manufacture of a medicament for treating cancer. In particular these cancers are selected from the group consisting of lung cancer, breast cancer, colorectal cancer, renal cancer, pancreatic cancer, head cancer, neck cancer, hereditary papillary renal cell carcinoma, childhood hepatocellular carcinoma, and gastric cancer. Furthermore, this invention provides a pharmaceutical composition for treating cancer selected from the group consisting of lung cancer, breast cancer, colorectal cancer, renal cancer, pancreatic cancer, head cancer, neck cancer, hereditary papillary renal cell carcinoma, childhood hepatocellular carcinoma, and gastric cancer comprising a compound of Formula I or a pharmaceutically acceptable salt thereof as an active ingredient.

It will be understood by the skilled reader that most or all of the compounds of the present invention are capable of forming salts. The compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499; S. M. Berge, et al., "Pharmaceutical Salts," Journal of Pharmaceutical Sciences, Vol 66, No. 1, January 1977. Preferred pharmaceutically acceptable salts of the compounds of the present invention are the methanesulfonate salts.

Preferred are compounds of Formula I wherein:

(a) $R^1$ is H;

(b) $R^1$ is methyl;

(c) $R^2$ is amino, dimethylamino, cyclopropyl, 6-methylpyridin-3-yl, pyrazol-4-yl, or a morpholin-4-yl of the formula:

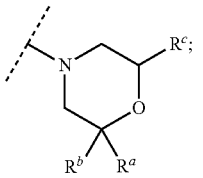

(d) $R^2$ is amino, dimethylamino, pyrazol-4-yl, or morpholin-4-yl;

(e) $R^2$ is pyrazo-4-yl;

(f) $R^1$ is methyl and $R^2$ is pyrazol-4-yl;

(g) $R^3$ is F;

(h) $R^1$ is methyl, $R^2$ is pyrazol-4-yl, and $R^3$ is F;

(i) $R^4$ is H, methyl, or morpholin-4-ylmethyl;

(j) $R^4$is H;

(k) $R^1$ is methyl, $R^2$ is pyrazol-4-yl, $R^3$ is F, and $R^4$ is H;

(l) $R^5$ is H;

(m) $R^5$ is F;

(n) $R^1$ is methyl, $R^2$ is pyrazol-4-yl, $R^3$ is F, $R^4$ is H, and $R^5$ is H;

(o) $R^1$ is methyl, $R^2$ is pyrazol-4-yl, $R^3$ is F, $R^4$ is H, and $R^5$ is F;

(p) X is CH═CH or CH═C($CH_3$);

(q) $R^1$ is methyl, $R^2$ is pyrazol-4-yl, $R^3$ is F, $R^4$ is H, $R^5$ is H, and X is CH═CH or CH═C($CH_3$);

(r) $R^1$ is methyl, $R^2$ is pyrazol-4-yl, $R^3$ is F, $R^4$ is H, $R^5$ is F, and X is CH═CH or CH═C($CH_3$);

(s) $R^1$ is methyl, $R^2$ is pyrazol-4-yl, $R^3$ is F, $R^4$ is H, $R^5$ is H or F, and X is CH═C($CH_3$);

(t) $R^1$ is methyl, $R^2$ is pyrazol-4-yl, $R^3$ is F, $R^4$ is H, $R^5$ is H, and X is CH═C($CH_3$); and (u) $R^1$ is methyl, $R^2$ is pyrazol-4-yl, $R^3$ is F, $R^4$ is H, $R^5$ is F, and X is CH═C($CH_3$).

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

Compounds of the present invention may be synthesized as illustrated in the following Scheme I, where X, $R^3$, $R^4$, and $R^5$ are as previously defined, and $R^{1'}$ and $R^{2'}$ are equal to or precursors of $R^1$ and $R^2$.

Scheme I

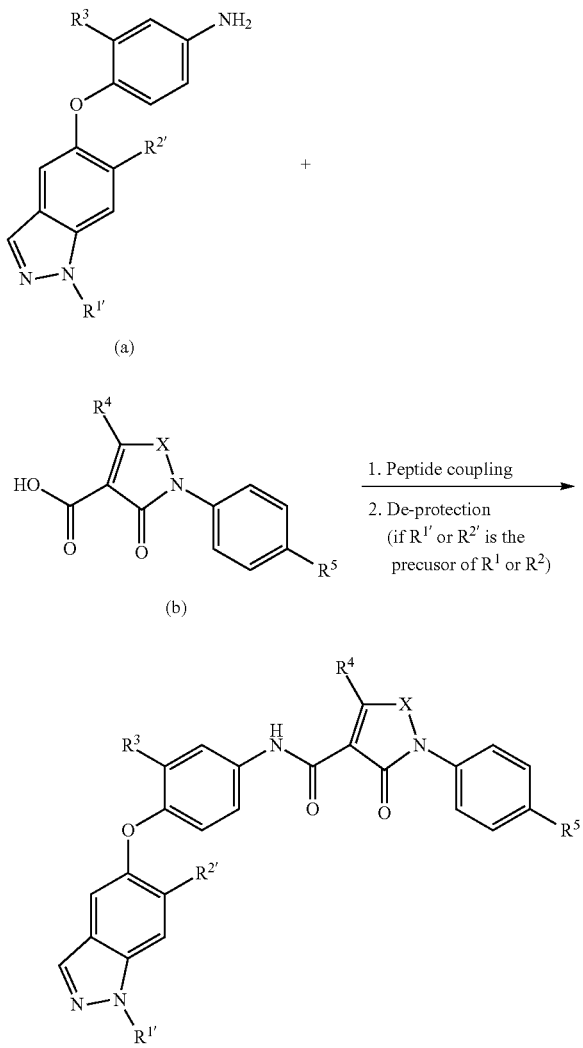

The compounds of the present invention can be made by standard peptide coupling conditions well known to the skilled artisan. A suitably substituted indazole aniline of formula (a) is reacted with an acid compound of formula (b), in the presence of a peptide coupling reagent such as 1-(3-dimethylaminopropyl)-3-ethylcarbodiimide hydrochloride (EDCI), 1-hydroxybenzotriazole hydrate (HOBt), an appropriate base such as N-methylmorpholine, N,N-diisopropylethylamine (DIPEA), or triethylamine (TEA), in a suitable solvent such as dichloromethane (DCM), N,N-dimethylformamide (DMF) or tetrahydrofuran (THF) to provide the desired amide of the present invention. If $R^{1'}$ is a suitable nitrogen protecting group such as tetrahydropyran (THP), or if $R^{2'}$ is a functional group protected by a nitrogen-protecting group, a de-protection step is needed to obtain the desired compound of the present invention.

Scheme II

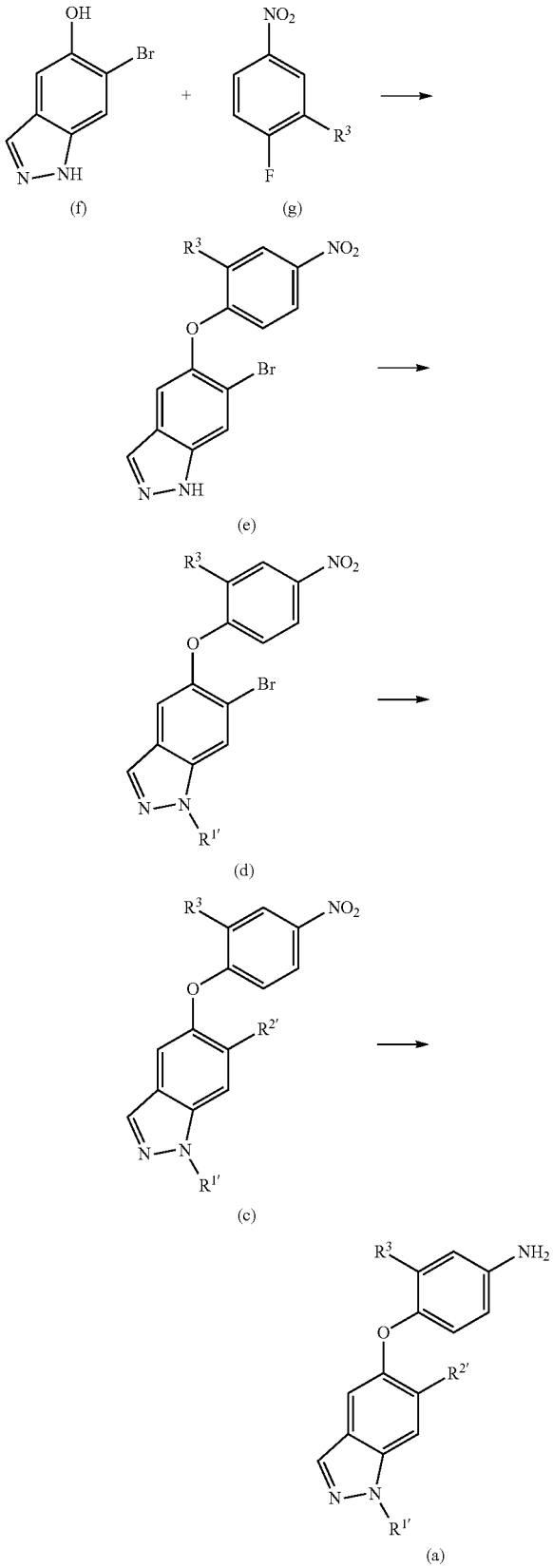

The compound of formula (a) can be prepared as illustrated in Scheme II, where $R^{1'}$, $R^{2'}$, and $R^3$ are as previously defined.

The compound of formula (f) can react with a properly substituted compound of formula (g) at elevated temperature, in the presence of a suitable base such as sodium bicarbonate in a proper solvent such as DMF to provide the compound of formula (e). The compound of formula (e) can be methylated with a proper methylation reagent such as methyl iodide in a suitable solvent such as THF with a suitable base such as potassium tert-butoxide to provide the compound of formula (d), where $R^{1'}$ is a methyl. The compound of formula (e) can also be protected with a suitable protecting reagent such as 2,3-dihydropyran (DHP) in a appropriate solvent such as THF, in the presence of an acid such as $CH_3SO_3H$ to provide the compound of formula (d), where $R^{1'}$ is a protecting group such as 2-tetrahydropyranyl. [Methods for introducing or removing protecting groups are well known in the art; see, for example, Greene and Wuts, Protective Groups in Organic Synthesis, 3rd Ed., John Wiley and Sons, New York, (1999)].

The compound of formula (d) can react under various transition-metal facilitated coupling conditions to provide the desired compound of formula (c) with a properly substituted $R^{2'}$ as previously defined. More specifically, if it is a carbon-carbon coupling, the compound of formula (c) can be made under coupling conditions such as a Suzuki coupling with a suitable boronic acid, an appropriate catalyst such as 1,1'-bis (diphenylphosphino)ferrocene palladium (II) chloride ($PdCl_2$(dppf)), and a proper base such as CsF in a suitable solvent such as 1,4-dioxane at elevated temperature. If it is a carbon-nitrogen coupling, the compound of formula (c) can be made under coupling conditions such as a Buchwald-Hartwig coupling with a proper nitrogen-containing reactant such as morpholine, a suitable ligand such as 2-di-tert-butylphosphino-2'-methylbiphenyl, a base such as KOH, and a catalyst such as tris(dibenzylideneacetone)-dipalladium (0) ($Pd_2(dba)_3$), in an appropriate solvent such as tert-butanol at elevated temperature. The coupling reaction can be carried out under conventional heating conditions or under microwave reaction conditions well known to the skilled artisan.

The compound of formula (c) can be reduced to an amino compound under various reduction conditions well known to the skilled artisan. More specifically, the compound of formula (c) can react with stannous chloride in a suitable solvent such as ethyl acetate (EtOAc)/ethanol (EtOH) at an elevated temperature to give the desired compound of formula (a). If $R^{1'}$ is a nitrogen-protecting group such as 2-tetrohydropyranyl, the protecting group will be cleaved. $R^{1'}$ will be a proton after the reduction.

The compound of formula (c) can also be reduced by reacting with N,N-dimethylhydrazine and $FeCl_3$ in a proper solvent such as methanol (MeOH), or $H_2$/palladium on carbon (Pd/C) in proper solvent such as EtOH. Both reduction conditions will only reduce the nitro group to an amino group, and will leave the nitrogen-protecting group, $R^{1'}$, untouched.

It is well known to the skilled artisan that reactions on nitrogen of some nitrogen-containing heterocycles such as indazole compounds could generate tautomers. The ratio of tautomers depends essentially on the mode of performing reactions and different conditions. Intermediates disclosed in this invention with nitrogen protecting groups such as THP may exist as regioisomers. In the compounds of the present invention, when $R^1$ is a proton, it may exist as a pair of fast exchanging tautomers as illustrated in Scheme III.

Scheme III

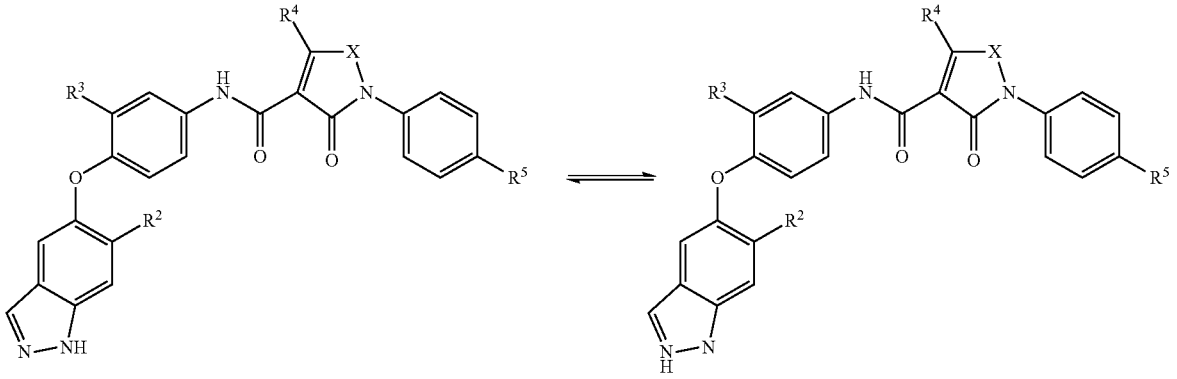

The following preparations and examples are named using ChemDraw® Ultra version 10.0.

Preparation 1

N-(4-Methoxy-2-methylphenyl)acetamide

To a solution of 4-methoxy-2-methylaniline (120 g, 0.88 mol) in DCM (400 mL) is added acetic acid anhydride (120 mL, 1.2 mol) dropwise. The reaction mixture is stirred at room temperature (RT) for 3 hours. After petroleum ether (PE) (1.6 L) is added, the slurry is stirred for another one hour. The precipitate is collected by filtration and is washed with PE to give the product as a pink solid (130 g, 82% yield). MS (m/z): 180.0 (M+H).

Preparation 2

N-(5-Bromo-4-methoxy-2-methylphenyl)acetamide

To a solution of N-(4-methoxy-2-methylphenyl)acetamide (130 g, 0.73 mol) in acetic acid (800 mL) is added bromine (42 mL, 0.8 mol) dropwise at 0° C. After addition, the resulting mixture is stirred at RT overnight. Saturated aqueous $NaHSO_3$ is added until a clear solution is obtained, and then a large amount of water (2.0 L) is added forming a precipitate. The precipitated solid is collected and washed with water to give the crude product (thin layer chromatography (TLC) solvent: DCM:EtOAc=10:1). The solid is dissolved in minimum amount of refluxing DCM, and then PE (about 10-20% volume of DCM used) is added. The resulting solution is cooled to RT. After 2 hours, the precipitated solid is collected and washed with PE to give a white product (108 g, 57% yield). MS (m/z): 260.0 (M+H).

Preparation 3

5-Bromo-4-methoxy-2-methylaniline

To a solution of N-(5-bromo-4-methoxy-2-methylphenyl) acetamide (108 g, 0.42 mol) in MeOH (400 mL) is added concentrated HCl (160 mL, 2 mol). After being heated at reflux overnight, the mixture is neutralized with aqueous $NaHCO_3$, and extracted with EtOAc (1200 mL). The organic phase is dried and concentrated to afford the product (76 g, 84% yield). MS (m/z): 216.0 (M+H).

Preparation 4

1-(5-Bromo-4-methoxy-2-methylphenyl)diazonium tetrafluoroborate

To a solution of 5-bromo-4-methoxy-2-methylaniline (76 g, 0.35 mol) in $HBF_4$ (48% wt, 140 mL) and $H_2O$ (280 mL) is added a solution of $NaNO_2$ (27.6 g, 0.4 mol) in $H_2O$ (60 mL) at 0° C. After the addition is completed, the reaction mixture is stirred at 0° C. for 30 minutes (min). The precipitate is filtered, washed with a small amount of ice water several times and dried to give the product (110 g, 99% yield). MS (m/z): 229.0 (M+H).

Preparation 5

6-Bromo-5-methoxy-1H-indazole 1-(5-Bromo-4-methoxy-2-methylphenyl)diazonium tetrafluoroborate (110 g, 0.35 mol) is added in one portion to a stirred mixture of KOAc (140.5 g, 1.43 mol) and 18-crown-6-ether (9.3 g, 0.035 mol) in $CHCl_3$ (800 mL) and stirred at RT overnight. The mixture is filtered and the solid is washed with DCM. The combined filtrate is concentrated and the residue is purified by silica gel column chromatography (DCM:MeOH=50:1) to give the product (10 g). The cake is added to THF (1600 mL) and the mixture is stirred at RT for one hour. The mixture is filtered and the filtrate is concentrated to give 10 g of the crude product (total yield 88%). MS (m/z): 229.0 (M+H).

Preparation 6

6-Bromo-5-hydroxy-1H-indazole

To a solution of 6-bromo-5-methoxy-1H-indazole (60 g, 0.265 mol) in DCM (1300 mL) is added a solution of $BBr_3$ (105 g, 0.42 mol) in DCM (200 mL) at 0° C. The reaction mixture is warmed to RT and stirred overnight. Then the reaction solution is quenched with MeOH at 0° C. The solvent is removed in vacuo and the residue is neutralized with $NaHCO_3$ solid. The mixture is partitioned by water (1500 mL) and EtOAc (1500 mL). The aqueous layer is extracted with EtOAc (1500 mL) two times. The combined organic layers are dried and concentrated to give crude product, which is purified by silica gel column chromatography (PE:THF=2:1) to give the desired product (42.5 g, 75% yield). MS (m/z): 215.0 (M+H).

Preparation 7

6-Bromo-5-(2-fluoro-4-nitrophenoxy)-1H-indazole

A mixture of 6-bromo-5-hydroxy-1H-indazole (7.0 g, 33.0 mmol), 3,4-difluoronitrobenzene (4.98 mg, 31.0 mmol), $NaHCO_3$ (2.5 g, 31.0 mmol) in DMF (100 mL) is stirred at 80° C. for 4 hours. Then LiCl (10% aqueous solution) is added and the solution is extracted with EtOAc. The organic phase is dried over anhydrous $MgSO_4$, filtered and concentrated. The residue is purified by silica gel column chromatography eluting with PE:DCM (1:1) to give the desired product (5.5 g, 46.6% yield). MS (m/z): 354.0 (M+H).

The following compound is prepared essentially by the method of Preparation 7:

| Prep. No. | Chemical name | Physical data MS (m/z) (M + H) |
|---|---|---|
| 8 | 6-Bromo-5-(4-nitrophenoxy)-1H-indazole | 336 |

Preparation 9

6-Bromo-5-(2-fluoro-4-nitrophenoxy)-1-(tetrahydro-2H-pyran-2-yl)-1H-indazole

To a solution of 6-bromo-5-(2-fluoro-4-nitrophenoxy)-1H-indazole (5.0 g, 14.2 mmol) in THF (50 mL) is added DHP (2.4 g, 28.5 mmol) and $CH_3SO_3H$ (1.0 g, 10.4 mmol). The resulting mixture is stirred at RT for 1 hour. Then EtOAc and aqueous $NaHCO_3$ solutions are added. The organic phase is separated, dried over anhydrous $MgSO_4$, filtered and concentrated. The residue is purified by silica gel column chromatography eluting with PE:EtOAc (5:1) to give the desired product (5.5 g, 89.0% yield). MS (m/z): 436.0 (M+H).

The following compound is prepared essentially by the method of Preparation 9:

| Prep. No. | Chemical name | Physical data MS (m/z) (M + H) |
|---|---|---|
| 10 | 6-Bromo-5-(4-nitrophenoxy)-1-(tetrahydro-2H-pyran-2-yl)-1H-indazole | 418.0 |

Preparation 11

6-Bromo-1-methyl-5-(4-nitrophenoxy)-1H-indazole

To a mixture of 6-bromo-5-(4-nitrophenoxy)-1H-indazole (2.68 g, 8.02 mmol) and KOH (600 mg, 10.69 mmol) in acetone (100 mL) cooled with an ice-water bath is added dropwise methyl iodide (0.55 mL, 8.83 mmol). After the reaction mixture is stirred at 0° C. for 2 hours, it is stirred at RT overnight. The solvent is removed, and the residue is purified by silica gel column chromatography eluting with PE:EtOAc (3:1) to give the product (1.50 g, 53.7% yield). MS (m/z): 348.0 (M+H).

The following compound is prepared essentially by the method of Preparation 11:

| Prep. No. | Chemical name | Physical data MS (m/z) (M + H) |
|---|---|---|
| 12 | 6-Bromo-5-(2-fluoro-4-nitrophenoxy)-1-methyl-1H-iadazole | 365.9 |

Alternatively, 6-bromo-5-(2-fluoro-4-nitrophenoxy)-1-methyl-1H-indazole (Preparation 12) may also be prepared in the following 3 step process:

2,4-Dibromo-5-hydroxy-benzaldehyde (50 g, 178.6 mmol), 1,2-difluoro-4-nitrobenzene (28.4 g, 178.6 mmol) and potassium carbonate (49.0 g, 357.2 mmol) are stirred in DMF (500 mL) at 60° C. for 2 hours. The reaction is quenched with water (1000 mL) and extracted with methyl tert-butylether (MTBE) (2×500 mL). The organic layer is washed with saturated sodium chloride aqueous solution (2×500 mL), dried with anhydrous sodium sulfate, and concentrated to obtain a yellow solid. The crude solid is recrystallized in EtOAc/PE (1:5) to give 2,4-dibromo-5-(2-fluoro-4-nitrophenoxy)benzaldehyde as a yellow solid (52.8 g, 70.6% yield).

2,4-Dibromo-5-(2-fluoro-4-nitrophenoxy)benzaldehyde (13.0 g, 31.0 mmol) is refluxed with methylhydrazine (4.3 g, 93 mmol) in THF (130 mL) for 2 hours. The reaction is quenched with water (150 mL) and extracted with MTBE (2×150 mL). The organic layer is washed with saturated sodium chloride aqueous solution (2×150 mL), dried with anhydrous sodium sulfate, and concentrated to obtain a solid. The crude solid is recrystallized in EtOAc/hexane to obtain 1-(2,4-dibromo-5-(2-fluoro-4-nitrophenoxy)benzylidene)-2-methylhydrazine as a yellow solid (10.6 g, 76.7% yield). MS (m/z): 447.9 (M+H).

1-(2,4-Dibromo-5-(2-fluoro-4-nitrophenoxy)benzylidene)-2-methylhydrazine (1.0 g, 2.2 mmol), cuprous chloride (22 mg, 0.2 mmol), potassium carbonate (0.638 g, 7.2 mmol), DMF (10 mL), and a stir bar are combined in a pressure tube under nitrogen. The cap is sealed and the tube is placed in an oil bath with stirring. The bath is heated to 100° C. over 30 min and held at 100° C. for 6 hours and then cooled to RT. The reaction mixture is poured into a separatory funnel containing MTBE (10 mL) and water (10 mL). The layers are separated and the aqueous layer is extracted with an additional portion of MTBE (10 mL). The organic layers are combined, and washed with water followed by saturated sodium chloride aqueous solution. The organic layer is dried over magnesium sulfate and concentrated to yield 0.70 g of crude product. The crude solid is dissolved in DCM and heptane, and then concentrated to remove DCM resulting in the formation of a slurry. The product is collected by filtration and dried under vacuum to give 6-bromo-5-(2-fluoro-4-nitrophenoxy)-1-methyl-1H-indazole as a solid (0.65 g, 79% yield). MS (m/z): 367.8 (M+H).

Preparation 13

6-Bromo-2-(tetrahydro-2H-pyran-2-yl)-2H-indazol-5-ol

To a solution of 6-bromo-5-hydroxy-1H-indazole (725.0 g, 3.4 mol) in THF (10.2 L) is added DHP (336.5 mL, 3.57 mol) and $CH_3SO_3H$ (65.4 g, 0.68 mol) at RT. The resulting mixture is stirred at RT for 22 hours. The reaction mixture is quenched with distilled water (6 L) and extracted with EtOAc (6 L).

Saturated aqueous $NaHCO_3$ solution (1100 mL) is added to adjust the pH to 8. After phase separation, the organic phase is washed with water (4 L) and then saturated aqueous sodium chloride (3 L), dried over anhydrous $Na_2SO_4$, filtered, and concentrated to give the product as a solid (1.64 kg, 99.3% yield). MS (m/z): 299.0 (M+H).

Preparation 14

6-Bromo-5-(2-fluoro-4-nitrophenoxy)-2-(tetrahydro-2H-pyran-2-yl)-2H-indazole

To a solution of 6-bromo-2-(tetrahydro-2H-pyran-2-yl)-2H-indazol-5-ol (1.475 kg, 4.96 mol) in DMF (5.3 L) is added 3,4-difluoronitrobenzene (1.18 kg, 7.45 mol) and $NaHCO_3$ (625.5 g, 7.45 mol) at RT. The reaction mixture is heated at 70° C. for 10 hours and then cooled to less than 20° C. Deionized (DI) water (7.9 L) is slowly added to the solution and the resulting slurry is stirred at 15° C. for one hour. The solid is collected by vacuum filtration, and the solid cake is washed with water (8 L). It is then air dried under vacuum on filter and is triturated with methyl MTBE (18.6 L) at reflux conditions for two hours. The slurry is then cooled to RT and the solid is collected by vacuum filtration. The solid cake is washed with MTBE (4 L×2) and dried in a vacuum oven at 35° C. to give the desired product (1.405 kg, 64.9% yield). MS (m/z): 436.0 (M+H).

Preparation 15

5-(2-Fluoro-4-nitrophenoxy)-6-(pyridine-4-yl)-1-(tetrahydro-2H-pyran-2-yl)-1H-indazole A mixture of 6-bromo-5-(2-fluoro-4-nitrophenoxy)-1-(tetrahydro-2H-pyran-2-yl)-1H-indazole (5.0 g, 11.5 mmol), 4-pyridineboronic acid (3.0 g, 24.3 mmol), $PdCl_2$(dppf) (1.8 g, 2.25 mmol) and CsF (5.0 g, 33.0 mmol) in 1,4-dioxane (100 mL) is stirred at 110° C. overnight. Then, aqueous $NH_4Cl$ and EtOAc are added. The organic phase is separated, dried over anhydrous $MgSO_4$ and concentrated. The residue is purified by silica gel column chromatography eluting with PE:EtOAc (3:1) to give the desired product (2.8 g, 56% yield). MS (m/z): 435.1 (M+H).

The following compounds are prepared essentially by the method of Preparation 15:

| Prep. No. | Chemical name | Physical data MS (m/z) (M + H) |
|---|---|---|
| 16 | 5-(2-Fluoro-4-nitrophenoxy)-6-(4-(methylsulfonyl)phenyl)-1-(tetrahydro-2H-pyran-2-yl)-1H-indazole | 512.1 |
| 17 | tert-Butyl 4-(5-(2-fluoro-4-nitrophenoxy)-1-(tetrahydro-2H-pyran-2-yl)-1H-indazol-6-yl)-1H-pyrazole-1-carboxylate | 524.1 |
| | 5-(2-Fluoro-4-nitrophenoxy)-6-(1H-pyrazol-4-yl)-1-(tetrahydro-2H-pyran-2-yl)-1H-indazole | 424.1 |
| 18 | 5-(2-Fluoro-4-nitrophenoxy)-6-(pyridin-3-yl)-1-(tetrahydro-2H- pyran-2-yl)-1H-indazole | 435.1 |
| 19 | 6-(1,3-Dimethyl-1H-pyrazol-5-yl)-5-(2-fluoro-4-nitrophenoxy)-1-(tetrahydropyran-2-yl)-1H-indazole | 452.1 |
| 20 | 5-(2-Fluoro-4-nitrophenoxy)-6-(2-methoxypyrimidin-5-yl)-1-(tetrahydropyran-2-yl)-1H-indazole | 466.1 |
| 21 | 5-(2-Fluoro-4-nitrophenoxy)-6-(2-methylpyridin-4-yl)-1-(tetrahydropyran-2-yl)-1H-indazole | 449.1 |
| 22* | 6-Cyclopropyl-5-(2-fluoro-4-nitrophenoxy)-2-(tetrahydro-2H-pyran-2-yl)-2H-indazole | 398 |

-continued

| Prep. No. | Chemical name | Physical data MS (m/z) (M + H) |
|---|---|---|
| 23 | tert-Butyl 4-(1-methyl-5-(4-nitrophenoxy)-1H-indazol-6-yl)-1H-pyrazole-1-carboxylate | 436.0 |
| | 1-Methyl-5-(4-nitrophenoxy)-6-(1H-pyrazol-4-yl)-1H-indazole | 336.0 |
| 24 | 5-(2-Fluoro-4-nitrophenoxy)-1-methyl-6-(2-methylpyridin-4-yl)-1H-indazole | 379.1 |
| 25 | 5-(2-Fluoro-4-nitrophenoxy)-1-methyl-6-(pyridin-3-yl)-1H-indazole | 365.1 |
| 26 | (tert-Butyl 4-(5-(2-fluoro-4-nitrophenoxy)-1-methyl-1H-indazol-6-yl)-1H-pyrazole-1-carboxylate | 454.0 |
| 27 | tert-Butyl 4-(5-(2-fluoro-4-nitrophenoxy)-1-methyl-1H-indazol-6-yl)-1H-pyrazole-1-carboxylate | 454.1 |
| | 5-(2-Fluoro-4-nitrophenoxy)-1-methyl-6-(1H-pyrazo1-4-yl)-1H-indazole | 354.1 |

*Reaction is carried out under microwave conditions at 95° C. for about 90 min.

Preparation 28

6-(2,6-Dimethylpyridin-4-yl)-5-(2-fluoro-4-nitrophenoxy)-1-(tetrahydropyran-2-yl)-1H-indazole To a solution of 6-bromo-5-(2-fluoro-4-nitrophenoxy)-1-(tetrahydropyran-2-yl)-1 1H-indazole (1.31 g, 3.0 mmol) in 1,4-dioxane (20 mL) is added bis(pinacolato)diboron (0.91 g, 3.6 mmol), $Pd_2(dba)_3$ (0.14 g, 0.2 mmol), tricyclohexylphosphine (0.1 g, 0.4 mmol), potassium acetate (KOAc) (0.59 g, 6.0 mmol) under $N_2$. After the reaction mixture is heated to reflux for 3 hours under $N_2$, it is cooled to RT. 4-Bromo-2,6-dimethylpyridine hydrobromide (0.8 g, 3.0 mmol), $PdCl_2$(dppf) (0. 16 g, 0.2 mmol), CsF (1.38 g, 9.0 mmol) are added under $N_2$. The resulting mixture is heated at reflux overnight under $N_2$. The solid is filtered off and the filtrate is concentrated. The residue is purified by silica gel column chromatography eluting with PE:EtOAc (from 5:1 to 1:1) to give the product (0.67 g, 48.3% yield). MS (m/z): 463.1 (M+H).

Preparation 29

4-(5-(2-Fluoro-4-nitrophenoxy)-1-(tetrahydro-2H-pyran-2-yl)-1H-indazol-6-yl)morpholine To a solution of 6-bromo-5-(2-fluoro-4-nitro-phenoxy)-1-(tetrahydropyran-2-yl)-1 H-indazole (8.0 g, 18 mmol) in tert-butanol (150 mL) and $H_2O$ (3.2 mL) is added $Pd_2(dba)_3$ (320 mg, 0.35 mmol), 2-di-tert-butylphosphino-2'-methylbiphenyl (480 mg, 1.54 mmol), KOH (3.2 g, 57 mmol) and morpholine (3.2 g, 36.7 mmol) under $N_2$. After the mixture is stirred at 70° C. for 2 hours under a $N_2$ atmosphere, it is filtered and the filtrate is concentrated. The residue is partitioned with EtOAc (100 mL) and saturated aqueous $NH_4Cl$ (30 mL). The organic layer is separated, dried over $MgSO_4$, and concentrated. The residue is purified by silica gel column chromatography eluting with PE:EtOAc (3:1) to give the product (4.5 g, 56.5% yield). MS (m/z): 443.1 (M+H).

The following compounds are prepared essentially by the method of Preparation 29:

| Prep. No. | Chemical name | Physical data MS (m/z) (M + H) |
|---|---|---|
| 30 | 5-(2-Fluoro-4-nitrophenoxy)-N,N-dimethyl-1-(tetrahydro-2H-pyran-2-yl)-1H-indazol-6-amine | 401.2 |
| 31 | N,N-Dimethyl-5-(4-nitrophenoxy)-1-(tetrahydro-2H-pyran-2-yl)-1H-indazol-6-amine | 383.1 |

Preparation 32

4-(5-(2-Fluoro-4-nitrophenoxy)-2-(tetrahydro-2H-pyran-2-yl)-2H -indazol-6-yl)-2-methylmorpholine (racemic)

To a 25 mL microwave vial is added 6-bromo-5-(2-fluoro-4-nitrophenoxy)-2-(tetrahydro-2H-pyran-2-yl)-2H-indazole (0.8 g, 1.8 mmol), 4,5-bis(diphenylphosphino)-9,9-dimethylxanthene (98 mg, 165 μmol) and $Pd_2(dba)_3$ (50 mg, 55 μmol). The mixture is suspended in toluene (12 mL, 113 mmol) and then 2-methylmorpholine hydrochloride (278 mg, 2.02 mmol) and sodium tert-butoxide (454 mg, 4.58 mmol) are added. The reaction mixture is heated at 150° C. for 25 min in a microwave reactor. The reaction mixture is then concentrated and the residue is purified on a silica gel column eluting with hexanes (A) and EtOAc (B), gradient from 90%(A): 10%(B) to 60%(A):40%(B) over 60 min then to 50%(A):50%(B) for 20 min to give an orange solid as the desired product (410 mg, 39% yield). MS (m/z): 457 (M+H).

The following compounds are prepared essentiallyby the method of Preparation 32:

| Prep. No. | Chemical name | Physical data MS (m/z) (M + H) |
|---|---|---|
| 33 | (2R)-4-(5-(2-Fluoro-4-nitrophenoxy)-2-(tetrahydro-2H-pyran-2-yl)-2H-indazol-6-yl)-2-methyhmorpholine | 456.8 |
| 34 | (2S,6R)-4-(5-(2-Fluoro-4-nitrophenoxy)-2-(tetrahydro-2H-pyran-2-yl)-2H-indazol-6-yl)-2,6-dimethylmorpholine | 470.8 |

Preparation 35

4-(5-(2-Fluoro-4-nitrophenoxy)-2-(tetrahydro-2H-pyran-2-yl)-2H-indazol-6-yl)-2,2-dimethylmorpholine 6-Bromo-5-(2-fluoro-4-nitrophenoxy)-2-(tetrahydro-2H-pyran-2-yl)-2H-indazole (1.5 g, 3.4 mmol) is added to a 50 mL Genevac Carousel® tube and is suspended into the amylene hydrate (10 mL, 91.4 mmol) and $N_2$ is bubbled in suspension. To the mixture is added 2-(di-tert-butylphosphino)-2'-methylbiphenyl (97.7 mg, 309 μmol), $Pd_2(dba)_3$ (94.5 mg, 103 μmol) and DI water (0.3 mL), and $N_2$ bubbling is continued for 10 min. To this mixture is added 2,2-dimethylmorpholine hydrochloride (1.04 g, 6.9 mmol) and a solution of KOH (617 mg, 11.0 mmol) dissolved in 0.3 mL of distilled water. The reaction mixture is heated at 80° C. for 2 hours and then cooled to RT. The mixture is then poured into EtOAc (300 mL), washed with distilled water (1×100 mL) and then saturated aqueous sodium chloride (100 mL). The combined aqueous layers are extracted with EtOAc (100 mL). The combined organic solution is dried with $Na_2SO_4$, filtered, and concentrated to dryness to give a gold solid. The solid is purified on a silica gel column eluting with hexanes (A) and EtOAc (B), gradient from 95%(A):5%(B) to 75%(A):25%(B) over 70 min to give a light yellow solid as the desired product (410 mg, 25% yield). MS (m/z): 470.8 (M+H).

Preparation 36

5-(2-Fluoro-4-nitrophenoxy)-6-(pyridine-4-yl)-1H-indazole

To a solution of 5-(2-fluoro-4-nitrophenoxy)-6-(pyridine-4-yl)-1-(tetrahydro-2H-pyran-2-yl)-1H-indazole (2.8 g, 6.45 mmol) in EtOH (30 mL) is added HCl (concentrated 5.0 mL). The mixture is stirred at 80° C. for 2 hours. Then aqueous $NaHCO_3$ and EtOAc are added. The organic phase is dried over anhydrous $MgSO_4$ and concentrated. The residue is purified by silica gel column chromatography eluting with PE:EtOAc (3:1) to give the desired product (1.95 g, 86.0% yield). MS (m/z): 351.0 (M+H).

Preparation 37

3-Fluoro-4-(6-(pyridine-4-yl)-1H-indazole-5-yloxy) aniline

A mixture of 5-(2-fluoro-4-nitrophenoxy)-6-(pyridine-4-yl)-1H-indazole (1.95 g, 4.5 mmol) and $SnCl_2.2H_2O$ (10.2 g, 45.3 mmol) in EtOAc/EtOH (200 mL/10 mL) is stirred at 80° C. for 2 hours. Then aqueous $NaHCO_3$ and EtOAc are added. The organic phase is dried over anhydrous $MgSO_4$ and concentrated. The residue is purified by silica gel column chromatography eluting with PE:EtOAc (2:1) to give the desired product (1.10 g, 61.0% yield). MS (m/z): 321.0 (M+H).

Preparation 38

3-Fluoro-4-(6-(4-(methylsulfonyl)phenyl)-1-(tetrahydro-2H-pyran-2-yl)-1H-indazol-5-yloxy)aniline To a solution of 5-(2-fluoro-4-nitrophenoxy)-6-(4-(methylsulfonyl)phenyl)-1-(tetrahydro-2H-pyran-2-yl)-1H-indazole (320 mg, 0.63 mmol) in EtOAc (50 mL) is added Pd/C (10%, 100 mg). The resulting mixture is degassed by evacuation and backfilled with $H_2$ three times. It is stirred under an atmosphere of $H_2$ at RT overnight. The solid is removed by filtration and the filtrate is concentrated. The residue is purified by silica gel column chromatography eluting with DCM:MeOH (20:1) to give the desired product (250 mg, 83% yield). MS (m/z): 482.1 (M+H).

The following compounds are prepared essentially by the method of Preparation 38:

| Prep. No. | Chemical name | Physical data MS (m/z) (M + H) |
|---|---|---|
| 39 | 3-Fluoro-4-(1-methyl-6-(2-methylpyridin-4-yl)-1H-indazol-5-yloxy)aniline | 349.1 |
| 40 | tert-Butyl 4-(5-(4-amino-2-fluorophenoxy)-1-methyl-1H-indazol-6-yl)-1H-pyrazole-1-carboxylate | 424 |

Preparation 41

4-(6-(1H-Pyrazol-4-yl)-1H-indazol-5-yloxy)-3-fluoroaniline

To a solution of 5-(2-fluoro-4-nitrophenoxy)-6-(1H-pyrazol-4-yl)-1-(tetrahydropyran-2-yl)-1H-indazole (900 mg, 2.13 mmol) and 4-[5-(2-fluoro-4-nitro-phenoxy)-1-(tetrahydropyran-2-yl)-1H-indazol-6-yl]-pyrazole-1-carboxylic acid tert-butyl ester (3.1 g, 5.92 mmol) in EtOAc/EtOH (75 mL/75 mL) is added stannous chloride dihydrate (10 g, 52.74 mmol). The reaction mixture is stirred at reflux overnight. After it is cooled and basified with saturated aqueous $NaHCO_3$ to pH 8-9, the mixture is extracted with EtOAc (100 mL). The organic phase is separated, dried over $MgSO_4$, and concentrated. The residue is purified by silica gel column chromatography eluting first with PE:EtOAc (1:1) and then with EtOAc to give the product (1.75 g, 71.0% yield). MS (m/z): 310.0 (M+H).

The following compounds are prepared essentially by the method of Preparation 41:

| Prep. No. | Chemical name | Physical data MS (m/z) (M + H) |
|---|---|---|
| 42 | 3-Fluoro-4-(6-(pyridin-3-yl)-1H-indazol-5-yloxy)aniline | 321.1 |
| 43 | 4-(6-(1,3-Dimethyl-1H-pyrazol-5-yl)-1H-indazol-5-yloxy)-3- fluoroaniline | 338.1 |
| 44 | 3-Fluoro-4-(6-morpholino-1H-indazol-5-yloxy)aniline | 329.1 |
| 45 | 4-[6-(2,6-Dimethylpyridin-4-yl)-1H-indazol-5-yloxy]-3-fluoroaniline | 349.1 |
| 46 | 3-Fluoro-4-[6-(2-methoxypyrimidin-5-yl)-1H-indazol-5-yloxy]-aniline | 352.1 |
| 47 | 5-(4-Amino-2-fluorophenoxy)-N,N-dimethyl-1H-indazol-6-amine | 287.1 |
| 48 | 3-Fluoro-4-(6-(2-methylpyridin-4-yl)-1H-indazol-5-yloxy)aniline | 335.1 |
| 49 | 5-(4-Aminophenoxy)-N,N-dimethyl-1H-indazol-6-amine | 269.1 |
| 50 | 4-(1-Methyl-6-(1H-pyrazol-4-yl)-1H-indazol-5-yloxy)aniline | 306.0 |
| 51 | 3-Fluoro-4-(1-methyl-6-(1H-pyrazol-4-yl)-1H-indazol-5-yloxy)aniline | 324.1 |
| 52 | 3-Fluoro-4-(1-methyl-6-(pyridin-3-yl)-1H-indazol-5-yloxy)aniline | 335.1 |

Preparation 53

4-(6-Cyclopropyl-2-(tetrahydro-2H-pyran-2-yl)-2H-indazol-5-yloxy)-3-fluoroaniline To a 25 mL glass vial is added 6-cyclopropyl-5-(2-fluoro-4-nitrophenoxy)-2-(tetrahydro-2H-pyran-2-yl)-2H-indazole (395 mg, 994 μmol) and MeOH (20 mL, 494 mmol). To the suspension is added N,N-dimethylhydrazine (756 μL, 9.94 mmol) and $FeCl_3$ (163 mg, 994 μmol). The vial is capped, and heated to 60° C. and stirred for 2 hours and then stirred at 50° C. overnight. The mixture is filtered over a Buchner funnel and the solid washed with MeOH (100 mL). The filtrate is collected and concentrated to give a brown/orange solid. The residue is purified on a silica gel column eluting with DCM (A) and a 10% MeOH in a DCM solution (B), gradient from 100% (A) to 85%(A): 15%(B) over 50 min to give a yellow solid as the title compound (358 mg, 98% yield). MS (m/z): 368 (M+H).

The following compounds are prepared essentially by the method of Preparation 53:

| Prep. No. | Chemical name | Physical data MS (m/z) (M + H) |
|---|---|---|
| 54 | 3-Fluoro-4-(6-(2-methylmorpholino)-2-(tetrahydro-2H-pyran- 2-yl)-2H-indazol-5-yloxy)aniline | 427 |
| 55 | 4-(6-(2,2-Dimethylmorpholino)-2-(tetrahydro-2H-pyran-2-yl)-2H-indazol-5-yloxy)-3-fluoroaniline | 441 |
| 56 | 3-Fluoro-4-(6-((R)-2-methylmorpholino)-2-(tetrahydro-2H-pyran-2-yl)-2H-indazol-5-yloxy)aniline | 427 |
| 57 | 4-(6-((2S,6R)-2,6-dimethylmorpholimo)-2-(tetrahydro-2H-pyran-2-yl)-2H-indazol-5-yloxy)-3-fluoroaniline | 441 |
| 58 | 3-Fluoro-4-(6-morpholino-2-(tetrahydro-2H-pyran-2-yl)-2H- indazol-5-yloxy)aniline | 413 |

Preparation 59

N-(Diphenylmethylene)-5-(2-fluoro-4-nitrophenoxy)-1-methyl-1H-indazol-6-amine

To a 10 mL microwave vial is added 6-bromo-5-(2-fluoro-4-nitrophenoxy)-1-methyl-1H-indazole (500 mg, 1.37 mmol), 4,5-bis(diphenylphosphino)-9,9-dimethylxanthene (73 mg, 123 μmol) and $Pd_2(dba)_3$ (38 mg, 41 μmol). The mixture is suspended in toluene (5 mL, 47 mmol) and benzophenone imine (272 mg, 1.5 mmol) and sodium tert-butoxide (203 mg, 2.05 mmol) are added. The mixture is heated at 150° C. for 20 min in a microwave reactor. After cooling, the reaction solution is concentrated to give a brown oil which is dissolved in DCM (150 mL) and washed with saturated aqueous sodium chloride (2×50 mL). The aqueous layers are combined and extracted with DCM (1×50 mL), dried with $Na_2SO_4$, filtered and concentrated to give a brown residue. The residue is purified on a silica gel column eluting with hexanes (A) and EtOAc (B), gradient from 85%(A): 15%(B) to 50%(A):50%(B) over 50 min to give a yellow solid material as the title compound (574 mg, 90.1% yield). MS (m/z): 467.2 (M+H).

Preparation 60

5-(4-Amino-2-fluorophenoxy)-N-benzhydryl-1-methyl-1H-indazol-6-amine

To a 100 mL round bottom flask is added N-(diphenylmethylene)-5-(2-fluoro-4-nitrophenoxy)-1-methyl-1H-indazol-6-amine (424 mg, 909 μmol) and EtOH (35 mL, 601 mmol). To the mixture is added ammonium formate (1000 mg, 15.9 mmol) followed by the addition of 10% Pd/C (300 mg, 141 μmol) and the reaction mixture is stirred at RT for 1 hour and heated at 45° C. for 15 min. The solvent is removed and the residue is dissolved in DCM (150 mL) and distilled water (100 mL). The organic layer is washed with distilled water (1 x 100 mL), and the combined aqueous layers are extracted with DCM (1 x 50 mL). The combined organic solution is dried with $Na_2SO_4$, filtered, and concentrated. The crude is purified on a silica gel column eluting with hexanes (A) and EtOAc (B), gradient from 90% (A)10% (B) to 40% (A):60% (B) over 90 min to give an off-white solid material as the title compound (204 mg, 51% yield). MS (m/z): 438.8 (M+H).

Preparation 61

1-Acetyl-6-bromo-1H-indazol-5-yl acetate

A mixture of 6-bromo-5-hydroxy-1H-indazole (25 g, 117 mmol) in acetic acid anhydride (75 mL) is heated at 110° C. with stirring for 2 hours. After it is cooled, diethyl ether (100 mL) is added. The precipitate is collected by filtration, washed with diethyl ether (30 mL), and dried under vacuum to afford the product (34 g, 98% yield). MS (m/z): 297.0 (M+H).

Preparation 62

Ethyl 5-hydroxy-1H-indazole-6-carboxylate

An autoclave is charged with 1-acetyl-6-bromo-1H-indazol-5-yl acetate (25 g, 84 mmol), TEA (25 g, 252 mmol), dichloro bis (benzonitrile) palladium ($Pd(PhCN)_2Cl_2$) (1.6 g, 4.2 mmol), 1,1 '-bis(diphenylphosphino)ferrocene (dppf) (4.7 g, 8.4 mmol) and EtOH (500 mL) is stirred at 130° C. under an atmosphere of CO for 8 hours. The reaction mixture is concentrated, and the residue is purified by silica gel column chromatography to afford the product (15.5 g, 90% yield). MS (m/z): 207.0 (M+H).

Preparation 63

Ethyl 5-hydroxy-1-(tetrahydro-2H-pyran-2-yl)-1H-indazole-6-carboxylate

To a solution of ethyl 5-hydroxy-1H-indazole-6-carboxylate (15.5 g, 75 mmol) in DCM (100 mL) and THF (100 mL) containing methanesulfonic acid (721 mg, 7.5 mmol) is added a solution of 3,4-dihydro-2H-pyran (6.6 g, 79 mmol) in DCM (20 mL) dropwise at RT. The resulting solution is stirred at RT overnight. After the solvent is removed, EtOAc (500 mL), saturated aqueous sodium chloride (500 mL) and $NaHCO_3$ (5 g) are added. The organic layer is separated, dried and concentrated. The residue is purified by silica gel column chromatography to afford the product (16.8 g, 77% yield). MS (m/z): 291.1 (M+H).

Preparation 64

Ethyl-5-(2-fluoro-4-nitrophenoxy)-1-(tetrahydro-2H-pyran-2-yl)-1H-indazole-6-carboxylate A mixture of ethyl 5-hydroxy-1-(tetrahydro-2H-pyran-2-yl)-1H-indazole-6-carboxylate (10.8 g, 37 mmol), 1,2-difluoro-4-nitrobenzene (7.1 g, 44 mmol), $NaHCO_3$ (7.4 g, 88 mmol) and DMF (100 mL) is stirred at 80° C. for 2 hours. After it is cooled to RT, water (400 mL) and PE (50 mL) are added and the mixture is stirred for 20 min. The precipitate is collected and dried under vacuum at 50° C. to afford the product (15 g, 95% yield). MS (m/z): 430.1 (M+H).

Preparation 65

5-(2-Fluoro-4-nitrophenoxy)-1-(tetrahydro-2H-pyran-2-yl)-1H-indazole-6-carboxylic acid To a solution of ethyl-5-(2-fluoro-4-nitrophenoxy)-1-(tetrahydro-2H-pyran-2-yl)-1H-indazole-6-carboxylate (22 g, 51.2 mmol) in THF (60 mL) and MeOH (60 mL) and $H_2O$ (10 mL) is added LiOH (3 g, 125 mmol). The resulting solution is stirred at RT for 1.5 hours and the organic solvents are removed. The aqueous residue is acidified with cold 6N HCl to pH 2, and extracted with EtOAc (150 mL). The organic phase is separated, dried, and concentrated. The residue is purified by silica gel column chromatography eluting with PE:EtOAc:acetic acid (100:100:1) to afford the product (19.5 g, 95% yield). MS (m/z): 402.1 (M+H).

Preparation 66 tert-Butyl 5-(2-fluoro-4-nitrophenoxy)-1-(tetrahydro-2H-pyran-2-yl)-1H-indazol-6-ylcarbamate A mixture of 5-(2-fluoro-4-nitrophenoxy)-1-(tetrahydro-2H-pyran-2-yl)-1H-indazole-6-carboxylic acid(590 mg, 1.47 mmol), diphenylphosphoryl azide (485 mg, 1.76 mmol), TEA (179 mg, 1.76 mmol), 4 Å molecular sieves (3 g) in tert-butanol (40 mL) is stirred at 80° C. overnight. The mixture is filtered and the filtrate is concentrated. The residue is purified by silica gel column chromatography eluting with PE/EtOAc (10:1) to give the desired product (400 mg, 65% yield). MS (m/z): 473.1 (M+H).

Preparation 67 tert-Butyl 5-(4-amino-2-fluorophenoxy)-1-(tetrahydro-2H-pyran-2-yl)-1H-indazol-6-ylcarbamate To a solution of tert-butyl 5-(2-fluoro-4-nitrophenoxy)-1-(tetrahydro-2H-pyran-2-yl)-1H-indazol-6-ylcarbamate (400 mg, 0.85 mmol) in EtOAc (50 mL) is added Pd/C (10%, 50 mg). The resulting mixture is degassed by evacuation and backfilled with $H_2$ three times. The mixture is stirred under an atmosphere of $H_2$ at RT overnight. The solid is removed by filtration and the filtrate is concentrated. The residue is purified by silica gel column chromatography eluting with DCM:MeOH (10:1) to give the desired product (300 mg, 80% yield). MS (m/z): 443.2 (M+H).

Preparation 68

5-(2-Fluoro-4-nitrophenoxy)-1-(tetrahydro-2H-pyran-2-yl)-N-(tetrahydro-2H-pyran-4-yl)-1H-indazole-6-carboxamide The solution of 5-(2-fluoro-4-nitrophenoxy)-1-(tetrahydro-2H-pyran-2-yl)-1H-indazole-6-carboxylic acid (0.5 g, 1.25 mmol), tetrahydropyran-4-ylamine (0.13 g, 1.25 mmol), EDCI (0.24 g, 1.25 mmol), HOBT (0.17 g, 1.25 mmol), N-methylmorpholine (0.5 mL) in DMF (5 mL) is stirred at RT overnight. Then the reaction mixture is partitioned with saturated aqueous $NH_4Cl$ (20 mL) and EtOAc (50 mL). The organic phase is separated, dried over $MgSO_4$, and concentrated. The residue is purified by silica gel column chromatography eluting with PE:EtOAc (1:1) to provide the product (0.49 g, 81.2% yield). MS (m/z): 485.1 (M+H).

Preparation 69

5-(4-Amino-2-fluorophenoxy)-1-(tetrahydro-2H-pyran-2-yl)-N-(tetrahydro-2H-pyran-4-yl)-1H-indazole-6-carboxamide To a solution of 5-(2-fluoro-4-nitrophenoxy)-1-(tetrahydro-2H-pyran-2-yl)-N-(tetrahydro-2H-pyran-4-yl)-1H-indazole-6-carboxamide (0.49 g, 1.0 mmol) in MeOH (50 mL) is added Pd/C (100 mg, 10% wt) under $N_2$. The resulting mixture is degassed by evacuation and backfilled with nitrogen.

Then the reaction mixture is stirred at RT under $H_2$ atmosphere overnight. The solid is removed by filtration and the filtrate is concentrated to give a crude product (0.42 g, 91.4% yield). MS (m/z): 455.1 (M+H).

Preparation 70

5-(Benzyloxy)-6-bromo-1H-indazole

To a solution of 6-bromo-5-hydroxy-1H-indazole (5 g, 23.5 mmol) in THF (50 mL) is added benzyl alcohol (3.05 g, 28.2 mmol), $PPh_3$ (7.39 g, 28.2 mmol) and diethylazodicarboxylate (4.46 mL, 28.2 mmol). After the reaction mixture is stirred at RT overnight, EtOAc (50 mL) and saturated aqueous $NH_4Cl$ (30 mL) are added. The organic phase is separated, dried over $MgSO_4$, and concentrated. The residue is purified by silica gel column chromatography eluting with PE:EtOAc (4:1) to provide the product (5.0 g, 70.2% yield). MS (m/z): 303.0 (M+H).

Preparation 71

5-(Benzyloxy)-6-bromo-1-(tetrahydro-2H-pyran-2-yl)-1H-indazole

To a solution of 5-(benzyloxy)-6-bromo-1H-indazole (5 g, 16.5 mmol) in THF (30 mL) and DCM (30 mL) is added 3,4-dihydro-2H-pyran (3 mL, 32.8 mmol) and methanesulfonic acid (1 mL, 15.3 mmol). After the reaction mixture is stirred at RT for 2 hours, EtOAc (50 mL) and saturated aqueous $NaHCO_3$ are added. The organic phase is separated, dried over $MgSO_4$, and concentrated. The residue is purified by silica gel column chromatography eluting with PE:EtOAc (4:1) to give the desired product (2.7 g, 42.2% yield). MS (m/z): 387.0 (M+H).

Preparation 72

5-(Benzyloxy)-1-(tetrahydro-2H-pyran-2-yl)-N-(tetrahydro-2H-pyran-4-yl)-1H-indazol-6-amine To a solution of 5-(benzyloxy)-6-brome-1-(tetrahydri-2H-pyran-2-yl)-1H-indazole (2 g, 5.16 mmol) in toluene (30 mL) is added tetrahydropyran-4-ylamine (800 mg, 7.91 mmol), palladium acetate (60 mg, 267 μmol), 2-dicyclohexylphosphino-2'-(N,N-dimethylamino)biphenyl (200 mg, 508 μmol) and sodium tert-butoxide (700 mg, 7.28 mmol) under $N_2$. After the reaction is stirred at 100° C. under $N_2$ for 1 hour, EtOAc (30 mL) is added and the reaction mixture is filtered. The filtrate is concentrated and the residue is purified by silica gel column chromatography eluting first with EtOAc:PE (1/1) and then EtOAc to give the desired product (1.87 g, 88.8% yield). MS (m/z): 408.2 (M+H).

Preparation 73

N-(5-(Benzyloxy)-1-(tetrahydro-2H-pyran-2-yl)-1H-indazol-6-yl)-N-(tetrahydro-2H-pyran-4-yl)acetamide To a solution of 5-(benzyloxy)-1-(tetrahydro-2H-pyran-2-yl)-N-(tetrahydro-2H-pyran-4-yl)-1H-indazol-6-amine (1.87 g, 4.59 mmol) in THF (30 mL) is added acetyl chloride (0.39 mL, 5.48 mmol) and $K_2CO_3$ (760 mg, 5.50 mmol). After the reaction mixture is heated to reflux for 30 min, $H_2O$ (20 mL) and EtOAc (30 mL) are added. The organic phase is separated, washed with saturated aqueous $NH_4Cl$, dried and concentrated to give the product (1.7 g, 82.4% yield). MS (m/z): 450.2 (M+H).

Preparation 74

N-(5-Hydroxy-1-(tetrahydro-2H-pyran-2-yl)-1H-indazol-6-yl)-N-(tetrahydro-2H-pyran-4-yl)acetamide To a solution of N-(5-(benzyloxy)-1-(tetrahydro-2H-pyran-2-yl)-1H-indazol-6-yl)-N-(tetrahydro-2H-pyran-4-yl) acetamide (1.7 g, 3.78 mmol) in EtOH (100 mL) and EtOAc (100 mL) is added Pd/C (1 g, 10% wt). After the reaction mixture is stirred at RT under $H_2$ overnight, it is filtered and the filtrate is concentrated. The residue is purified by silica gel column chromatography eluting first with PE:EtOAc (1:1) and then EtOAc to give the product (1.2 g, 88.2% yield). MS (m/z): 360.2 (M+H).

Preparation 75

N-(5-(2-Fluoro-4-nitrophenoxy)-1-(tetrahydro-2H-pyran-2-yl)-1H-indazol-6-yl)-N-(tetrahydro-2H-pyran-4-yl)acetamide To a solution of N-(5-hydroxy-1-(tetrahydro-2H-pyran-2-yl)-1H-indazol-6-yl)-N-tetrahydro-2H-pyran-4-yl)acetamide (1.2 g, 3.34 mmol) in DMF (30 mL)is added 1,2-difluoro-4-nitrobenzene (0.64 g, 4.02 mmol) and $Cs_2CO_3$ (1.63 g, 5.00 mmol). After the reaction mixture is stirred at 100° C. for 2 hours, EtOAc (60 mL) and saturated aqueous $NH_4Cl$ are added. The organic phase is separated, dried over $MgSO_4$ and concentrated. The residue is purified by silica gel column chromatography eluting first with PE:EtOAc (1:1) and then EtOAc to give the product (1.44 g, 86.5% yield). MS (m/z): 499.2 (M+H).

Preparation 76

5-(4-Amino-2-fluorophenoxy)-N-(tetrahydro-2H-pyran-4-yl)-1H-indazol-6-amine

The title compound is prepared essentially by the method of Preparation 41. MS (m/z): 343.1 (M+H).

Preparation 77

5-(Benzyloxy)-6-(6-methylpyridin-3-yl)-1-(tetrahydro-2H-pyran-2-yl)-1H-indazole

To a solution of 5-(benzyloxy)-6-bromo-1-(tetrahydro-2H-pyran-2-yl)-1H-indazole (4 g, 10.3 mmol) in 1,4-dioxane (25 mL) is added bis(pinacolato)diboron (3 g, 11.8 mmol), dppf (0.3 g, 541 μmol), $PdCl_2$(dppf) (0.42 g, 514 μmol) and KOAc (2 g, 20.4 mmol) under $N_2$. After the reaction mixture is stirred at reflux for 5 hours, 5-bromo-2-methylpyridine (2.1 g, 12.2 mmol), tetrakis(triphenylphosphine)palladium (Pd$(PPh_3)_4$) (0.6 g, 519 μmol) and $Cs_2CO_3$ (4 g, 12.3 mmol) are added and the mixture is stirred at reflux overnight. The reaction mixture is cooled and filtered, the filtrate is concentrated. The residue is purified by silica gel column chromatography eluting with PE:EtOAc (2:1) to give the product (1.9 g, 46.0% yield). MS (m/z): 400.1 (M+H).

Preparation 78

6-(6-Methylpyridin-3-yl)-1-(tetrahydro-2H-pyran-2-yl)-1H-indazol-5-ol

To a solution of 5-(benzyloxy)-6-(6-methylpyridin-3-yl)-1-(tetrahydro-2H-pyran-2-yl)-1H-indazole (1.44 g, 3.60 mmol) in EtOH (50 mL) and EtOAc (50 mL) is added Pd/C (500 mg, 10% wt) under $N_2$. The resulting mixture is degassed by evacuation and backfilled with nitrogen. Then the reaction mixture is stirred at RT under $H_2$ atmosphere overnight. The reaction mixture is filtered. The filtrate is concentrated to give the product (982 mg, 88.0% yield). MS (m/z): 310.1 (M+H).

Preparation 79

5-(2-Fluoro-4-nitrophenoxy)-6-(6-methylpyridin-3-yl)-1-(tetrahydro-2H-pyran-2-yl)-1H-indazole The title compound is essentially made by the same method of Preparation 75. MS (m/z): 449.2 (M+H).

Preparation 80

3-Fluoro-4-(6-(6-methylpyridin-3-yl)-1H-indazol-5-yloxy)aniline

The title compound is prepared essentially by the method of Preparation 41. MS (m/z): 335.1 (M+H).

Preparation 81

1-(4-Bromo-2-fluorophenoxy)-2-fluoro-5-methyl-4-nitrobenzene

The title compound is prepared essentially by the same method of Preparation 75. $^1$H NMR ($d_6$-dimethylsulfoxide (DMSO)) δ 8.20 (d, 1H), 7.80 (d, 1H), 7.42 (d, 1H), 7.30(d, 1H), 7.10(d, 1H).

Preparation 82

4-(4-Bromo-2-fluorophenoxy)-5-fluoro-2-methylaniline

The title compound is prepared essentially by the method of Preparation 53. MS (m/z): 315.8 (M+H).

Preparation 83

5-(4-Bromo-2-fluorophenoxy)-6-fluoro-1H-indazole

To a suspension of 4-(4-bromo-2-fluorophenoxy)-5-fluoro-2-methylaniline (5.2 g, 16.6 mmol) in water (100 mL) is added fluoroboric acid (6.06 g, 33.1 mmol) at RT. The solution is cooled to 0° C. and $NaNO_2$ (1.71 g, 24.8 mmol) in water (2 mL) is added. The reaction is stirred at 0° C. for 40 min. $CHCl_3$ (200 mL) is added. The organic phase is separated, dried over $Na_2SO_4$, and filtered. To the filtrate is added KOAc (7.31 g, 74.5 mmol) and 18-crown-6-ether (0.218 g, 0.82 mmol). The reaction is stirred at RT for 1 hour. The reaction mixture is washed with saturated aqueous sodium chloride, dried over $Na_2SO_4$, filtered and evaporated. The residue is washed with DCM and filtered to offer the desired product as a light yellow solid. The filtrate is purified by chromatography eluting with DCM then EtOAc:hexane (1:1) to give additional desired product. Both portions of the solid are combined to offer the desired product (3.2 g, 59% yield). MS (m/z): 324.8 (M+H).

Preparation 84

5-(4-Bromo-2-fluorophenoxy)-6-fluoro-1-(tetrahydro-2H-pyran-2-yl)-1H-indazole

The title compound is prepared essentially by the method of Preparation 9. MS (m/z): 410.8 (M+H).

Preparation 85

N-(Diphenylmethylene)-3-fluoro-4-(6-fluoro-1-(tetrahydro-2H-pyran-2-yl)-1H-indazol-5-yloxy)aniline The mixture of 5-(4-bromo-2-fluorophenoxy)-6-fluoro-1-(tetrahydro-2H-pyran-2-yl)-1H-indazole (0.97 g, 2.37 mmol), benzophenone imine (0.64 g, 3.56 mmol), 4,5-bis (diphenylphosphino)-9,9-dimethylxanthene (0.10 g, 0.075 mol), $Cs_2CO_3$ (1.16 g, 3.56 mmol), $Pd_2(dba)_3$ (0.11 g, 0.12 mmol) in 1,4-dioxane (20 mL) is purged with nitrogen, heated to 100° C. and stirred overnight. The reaction mixture is cooled to RT, extracted with EtOAc, washed with saturated aqueous sodium chloride, dried over $Na_2SO_4$, filtered and concentrated (1.45 g). MS (m/z): 510 (M+H).

Preparation 86

3-Fluoro-4-(6-fluoro-1-(tetrahydro-2H-pyran-2-yl)-1H-indazol-5-yloxy) aniline

To a solution of N-(diphenylmethylene-3-fluoro-4-(6fluoro-1-(tetrahydro-2H-pyran-2-yl)-1H-indazol-5-yloxy) aniline (1.45 g, 2.85 mmol) in THF (30 mL) and water (5 mL) is added 1N aqueous HCl (5.69 mL, 5.69 mmol). The reaction is stirred at RT for 2 hours. EtOAc is added and the mixture is washed with saturated aqueous $NaHCO_3$ solution, saturated aqueous sodium chloride, dried over $Na_2SO_4$, filtered and evaporated. The residue is purified by chromatography eluting with DCM then EtOAc:hexane (1:1) to offer the desired product as a pale gel (0.53 g, 54% yield). MS (m/z): 346 (M+H).

Preparation 87

Ethyl 5-(2-fluoro-4-nitrophenoxy)-1-(tetrahydro-2H-pyran-2-yl)-1H-indazole-6-carboxylate The title compound is essentially made by the same method of Preparation 75. MS (m/z): 430.1 (M+H).

Preparation 88

Ethyl 5-(2-fluoro-4-nitrophenoxy)-1H-indazole-6-carboxylate

To a solution of ethyl 5-(2-fluoro-4-nitrophenoxy)-1-(tetrahydro-2H-pyran-2-yl)-1H-indazole-6-carboxylate (15 g, 35 mmol) in DCM (300 mL) is added trifluoroacetic acid (TFA) (30 mL), and stirred at RT overnight. DCM is evaporated. The residue is partitioned between EtOAc (800 mL) and 5% aqueous $NaHCO_3$ (400 mL). The organic layer is washed with saturated aqueous sodium chloride, dried over $MgSO_4$, and concentrated. The residue is purified by silica gel column chromatography eluting with PE:acetone (5:1) to afford the product (10.4 g, 86% yield). MS (m/z): 346.1 (M+H).

Preparation 89

Ethyl 5-(2-fluoro-4-nitrophenoxy)-1-methyl-1H-indazole-6-carboxylate

The title compound is prepared essentially by the method of Preparation 11: MS (m/z): 360.1 (M+H).

Preparation 90

5-(2-Fluoro-4-nitrophenoxy)-1-methyl-1H-indazole-6-carboxylic acid

To a solution of ethyl 5-(2-fluoro-4-nitrophenoxy)-1-methyl-1H-indazole-6-carboxylate (1.19 g, 3.5 mmol) in THF/$H_2O$ (15 mL/5 mL) is added LiOH (0.2 g, 8.3 mmol). After the reaction is stirred at RT for 2 hours, the solvents are removed. The residue is acidified with 2N HCl to pH 5, and extracted with EtOAc (50 mL). The organic phase is washed with saturated aqueous sodium chloride, dried and concentrated to give the product (1.1 g, 100% yield). MS (m/z): 332.0 (M+H).

Preparation 91 tert-Butyl 5-(2-fluoro-4-nitrophenoxy)-1-methyl-1H-indazol-6-ylcarbamate

The suspension of 5-(2-fluoro-4-nitrophenoxy)-1-methyl-1H-indazole-6-carboxylic acid (1.1 g, 3.3 mmol), diphenyl phosphoryl azide (0.91 g, 3.3 mmol), TEA (0.33 g, 3.3 mmol) and 4 Å molecular sieve (2.5 g) in tert-butanol (50 mL) is heated at reflux overnight. Then the solid is filtered off and the filtrate is concentrated. The residue is partitioned between saturated aqueous sodium chloride (40 mL) and EtOAc (100 mL). The organic phase is separated, dried and concentrated and the residue is purified by silica gel column chromatography eluting with PE:acetone (4:1) to give the product (0.64 g, 47.9% yield). MS (m/z): 403.1 (M+H).

Preparation 92 tert-Butyl 5-(4-amino-2-fluorophenoxy)-1-methyl-1H-indazol-6-ylcarbamate

The title compound is prepared essentially by the method of Proparation 38. MS (m/z): 373.1 (M+H).

Preparation 93

5-(5-(Benzyloxy)-1-(tetrahydro-2H-pyran-2-yl)-1H-indazol-6-yl)pyridin-2-amine to a solution of 5-(benzyloxy)-6-bromo-1-(tetrahydri-2H-pyran-2yl)-1H-indazole (1.5 g, 3.87 mmol) in 1,4-dioxane (50 mL) is added 5-(4,4,5,5-tetramethyl-1,3,2-dioxaborolan-2-yl)pyridin-2-amine (1 g, 4.54 mmol), $Pd(PPh_3)_4$ (200 mg, 173 μmol) and $Cs_2CO_3$ (5 g, 10.6 mmol). After the reaction mixture is stirred at reflux overnight, it is partitioned between EtOAc (100 mL) and saturated aqueous $NH_4Cl$ (50 mL). The organic phase is separated, dried and concentrated. The residue is purified by silica gel column chromatography eluting with DCM:MeOH (15:1) to give the product (0.80 g, 51.5% yield). MS (m/z): 401.1 (M+H).

Preparation 94 tert-Butyl 5-(5-(benzyloxy)-1-(tetrahydro-2H-pyran-2-yl)-1H-indazol-6-yl)pyridin-2-ylcarbamate To a solution of 5-(5-(benzyloxy)-1-(tetrahydro-2H-pyran-2-yl)-1H-indazol-6-yl)pyridin-2-amine (310 mg, 774 μmol) in THF (20 mL) is added di-tert-butyldicarbonate (250 mg, 1.13 mmol) and TEA (1 mL, 7.17 mmol). After the reaction mixture is stirred at RT for 3 hours, it is partitioned between EtOAc (50 mL) and saturated aqueous $NH_4Cl$ (20 mL). The organic phase is separated, dried and concentrated. The residue is purified by silica gel column chromatography eluting with PE:EtOAc (3:1) to give the product (260 mg, 67.1% yield). MS (m/z): 501.2 (M+H).

Preparation 95 tert-Butyl 5-(5-hydroxy-1-(tetrahydro-2H-pyran-2-yl)-1H-indazol-6-yl)pyridin-2-ylcarbamate To a solution of tert-butyl 5-(5-(benzyloxy)-1-(tetrahydro-2H-pyran-2-yl)-1H-indazol-6-yl)pyridin-2-ylcarbamate (260 mg, 519 μmol) in EtOH (25 mL) and EtOAc (25 mL) is added Pd/C (100 mg, 10% wt) under $N_2$. The resulting mixture is degassed by evacuation and backfilled with nitrogen. Then the reaction mixture is stirred at RT under $H_2$ atmosphere for 6 hours. The reaction mixture is filtered. The filtrate is concentrated to give the product (200 mg, 93.8% yield). MS (m/z): 411.1 (M+H).

Preparation 96 tert-Butyl 5-(5-(2-fluoro-4-nitrophenoxy)-1-(tetrahydro-2H-pyran-2-yl)-1H-indazol-6-yl)pyridin-2-ylcarbamate The title compound is essentially made by the same method of Preparation 75. MS (m/z): 550.2 (M+H).

Preparation 97 tert-Butyl 5-(5-(4-amino-2-fluorophenoxy)-1-(tetrahydro-2H-pyran-2-yl)-1H-indazol-6-yl)pyridin-2-ylcarbamate The title compound is prepared essentially by the method of Preparation 38. MS (m/z): 520.2 (M+H).

Preparation 98 tert-Butyl 4-(5-(2-fluoro-4-nitrophenoxy)-1-methyl-1H-indazol-6-yl)-1H-pyrazole-1-carboxylate 5-(2-Fluoro-4-nitrophenoxy)-1-methyl-6-(1 H-pyrazol-4-yl)-1H-indazole (1.56 g, 4.42 mmol) in DCM (15.6 mL) is added di-tert-butyldicarbonate (1.09 mL, 4.83 mmol). The mixture is stirred for 30 min. HPLC shows the reaction is complete. The solvent is removed under reduced pressure. Then MTBE (5 mL) is added. The solution is cooled with ice water bath and stirred for 15 min, then filtered to give the title compound as a solid (0.764 g, 48.9%).

Preparation 99

6-Bromo-5-(2-fluoro-4-nitrophenoxy)-1H-indazole

To a 3000 mL flask is added 6-bromo-5-(2-fluoro-4-nitrophenoxy)-2-(tetrahydro-2H-pyran-2-yl)-2H-indazole (250 g, 573.1 mmol) followed by MeOH (1000 mL) and $MeSO_3H$ (1 12.71 mL,1.72 mol) and heated to 50° C. for 14 hours. Solid crystallizes out of solution. The mixture is then cooled to RT. The reaction mixture is concentrated under vacuum at 45° C. to dryness to get solid. The solid is diluted with DCM (2000 mL) and treated with water (1000 mL) and 5N NaOH (about 350 mL) until the pH is 8-9. The organic layer is separated and the solvent is removed followed by azeotrope with toluene to give 195.6 g of the yellow solid material. MS (m/z): 354.0 (M+H).

Preparation 100

6-Bromo-5-(2-fluoro-4-nitrophenoxy)-1-methyl-i H-indazole

To a 4000 mL flask is added 6-bromo-5-(2-fluoro-4-nitrophenoxy)-1H-indazole (230 g, 653.2 mmol), DMF (3000 mL), and $K_2CO_3$ (135.41 g, 979.78 mmol). The reaction mixture is cooled to 4.5° C. with an ice bath. To the mixture is added methyl iodide (92.71 g, 653.19 mmol) and the reaction is allowed to stir for 20 min at the same temperature. The reaction is allowed to warm to RT and stir for 13 hours. The reaction mixture is monitored by liquid chromatography mass spectrometry. Additional methyl iodide (50 g) and $NaHCO_3$ (33 g) are added and the reaction mixture is stirred at RT until the reaction is completed. The reaction mixture is divided into two portions labeled (A) and (B), and each one is quenched with water (1 L) followed by extraction with EtOAc (1 L) causing some solids to form. The combined solids from (A) and (B) are collected by vacuum filtration to give 70 g of crude weight having about 90% 6-bromo-5-(2-fluoro-4-nitrophenoxy)-1-methyl-1H-indazole (which is the desired isomer) and 8% 6-bromo-5-(2-fluoro-4-nitrophenoxy)-2-methyl-2H-indazole isomers. This solid is then triturated with 1000 mL of DCM and 750 mL of MeOH overnight (about 14 hours). The solid is collected by filtration and rinsed with fresh DCM (100 mL) to give 55.5 g of desired material labeled (C). The mother liquor is concentrated and labeled (D). The organic layer from (A) and (B) are separated and concentrated. The residues from (A) and (B) are combined to give 185 g of crude as an orange solid labeled (E).

The crude compound (E) is dissolved in MeOH and DCM, and then the solution is divided into 3 portions. 600 g of silica gel is mixed with each portion of solution, and then the silica gel mixture is loaded into seven 270 g size empty cartridges. Seven 1.5 kg ISCO® columns are used with solvent system starting with 25% EtOAc in hexanes, then it is switched to 50% EtOAc in hexanes to give 62 g of the desired compound as a yellow powder labeled (F). After 7 runs, there are some mixed fractions of 6-bromo-5-(2-fluoro-4-nitrophenoxy)-1-methyl-1H-indazole and 6-bromo-5-(2-fluoro-4-nitrophenoxy)-2-methyl-2H-indazole isomers. The fractions are combined and combined with mother liquor (D) from the procedure described above to give 17 g of the mixture. The mixture is dissolved in MeOH and DCM, mixed with 170 g of silica into the solution, and run on a 1.5 kg column to give 10 g of a yellow powder as the desired product labeled (G). Total yield (55.5 g (C), 62 g (F), and 10 g (G)) is 127.5 g.

Preparation 101 tert-Butyl 4-(5-(2-fluoro-4-nitrophenoxy)-1-methyl-1H-indazol-6-yl)-1H-pyrazole-1-carboxylate To a 12 L round bottom flask equipped with overhead agitation, a thermocouple, heating mantle, condenser, and subsurface nitrogen sparge is added 1,4-dioxane (7.44 L) and water (1.67 L). The solution is purged with $N_2$ (inlet tube). Next 6-bromo-5-(2-fluoro-4-nitrophenoxy)-1-methyl-1H-indazole (595 g, 1.63 mol) is added and the solution is purged with $N_2$ again. tert-Butyl 4-(4,4,5,5-tetramethyl-1,3,2-dioxaborolan-2-yl)-1H-pyrazole-1-carboxylate (717.02 g, 2.44 mol), potassium phosphate tribasic N-hydrate (689.8 g, 3.25 mol), and 1,1'-Bis(di-tert-butylphosphino)ferrocene (7.71 g, 16.25 mmol) are added. Finally, $Pd_2(dba)_3$ (7.44 g, 8.13 mmol) is added. The solution is purged for 15 min and then heated at 60° C. for 12 hours. The reaction is not complete and more $Pd_2(dba)_3$ (7.44 g, 8.13 mmol) is added. The solution is again heated at 60° C. for 3 additional hours and the reaction is complete. 1,4-Dioxane is then removed (Buchi® bath temp 60° C.) and the residue is re-dissolved in 10 volumes (6 L) of DCM. Water (3 L) is added and then the layers are separated. The organic solution is dried over $Na_2SO_4$, filtered and concentrated to a dark oil (835 g). The material is not purified and is forward processed to the next step. The material is about 60% desired product and about 40% 5-(2-fluoro-4-nitrophenoxy)-1-methyl-6-(1H-pyrazol-4-yl)-1H-indazole. The crude obtained is reprotected in the next step. It is assumed that 50% of the crude product is the 5-(2-fluoro-4-nitrophenoxy)-1-methyl-6-(1H-pyrazol-4-yl)-1H-indazole.

To a 22 L round bottom flask with overhead agitation, thermocouple, 1 L addition funnel, $N_2$ purge, and cooling bath is added a solution of crude 5-(2-fluoro-4-nitro-phenoxy)-1-methyl-6-(1H-pyrazol-4-yl)-1H-indazole (835 g, 1. 18 mol) in DCM (6 L) of. di-tert-butyldicarbonate (283.69 g, 1.30 mol) dissolved in DCM (350 mL) of is added to an addition funnel. The solution is added dropwise over 48 min. After the reaction is complete, DCM is removed by rotary evaporation to give a dark oil. To the dark oil is added MTBE (2.5 L) and the oily solution is cooled to about 0-5° C. The solution is seeded with material obtained in Preparation 98. After seeding, crystallization is observed and the resulting slurry is stirred for 30-40 min. The pale yellow slurry is filtered over a polypropylene pad and the cake is washed with cold (0-5° C.) MTBE (1.5 L). The solids are dried in a 40° C. vacuum oven overnight to give the desired product (443 g, 60% crude yield). MS (m/z): 354.0 (M+H). The material is shown to be about 93-95% pure by HPLC and is therefore forward processed.

Preparation 102 tert-Butyl 4-(5-(4-amino-2-fluorophenoxy)-1-methyl-1H-indazol-6-yl)-1H-pyrazole-1-carboxylate To a 3 gallon tank is added tert-butyl 4-(5-(2-fluoro-4-nitrophenoxy)-1-methyl-1H-indazol-6-yl)-1H-pyrazole-1-carboxylate (433.0 g, 952.8 mmol) followed by THF (6.5 L) and Pd/C (21.65 g, 10% Pd/C and 21.65 g, 5% Pd/C). The mixture is heated to 35° C. under hydrogen gas for 2 hours. The reaction is then cooled to RT and allowed to stir under hydrogen gas overnight, then is heated to 40° C. under hydrogen gas for seven hours. An additional 2 g Pd/C (1 g, 10% Pd/C and 1 g, 5% Pd/C) is added and stirred under hydrogen gas for another hour and cooled to RT. The mixture is again stirred under hydrogen gas overnight and the reaction is completed. The mixture is filtered over a combination of GFF® and Watman® paper. The filtrate is concentrated to a slightly yellow solid (446 g, 110% recovery).

Preparation 103

Methyl 2-oxo-1,2-dihydropyridine-3-carboxylate

To a flask is added 2-hydroxynicotinic acid (10 g, 72 mmol), concentrated $H_2SO_4$ (2 mL) and MeOH (400 mL), followed by toluene (80 mL). The reaction mixture is heated to reflux overnight with a Dean-Stark trap. After cooling to RT, the mixture is filtered and the filtrate is concentrated. The residue is dissolved in DCM (200 mL), neutralized with saturated aqueous $NaHCO_3$ to pH 7 and extracted with DCM (200 mL) for three times. The combined organic phases are dried and concentrated to give the desired product (8.2 g, 74% yield). MS (m/z): 153.9 (M+H).

Preparation 104

Methyl 1-(4-fluorophenyl)-2-oxo-1,2-dihydropyridine-3-carboxylate

To a mixture of methyl 2-oxo-1,2-dihydropyridine-3-carboxylate (6.0 g, 39 mmol), 4-fluorophenylboronic acid (16.3 g, 116 mmol), cupric acetate (14 g, 78 mmol) and pyridine (12 g, 0.156 mol) in DCM (300 mL) is added 4 Å molecular sieves (5 g). The reaction mixture is stirred at RT overnight open to air. After the solids are filtered and washed with water, the filtrate is extracted with DCM (100 mL). The organic layer is dried over $MgSO_4$ and concentrated. The residue is purified by silica gel column chromatography eluting with PE:DCM (2:1 to 0:1) to give the product (9.6 g, 100% yield). MS (m/z): 248.0 (M+H).

Preparation 105

Ethyl 2-(4-fluorophenyl)hydrazinecarboxylate

To a solution of 4-fluorophenylhydrazine hydrochloride (2 g, 12.05 mmol) in THF (60 mL) is added DIPEA (6 mL, 34.40 mmol), ethyl chloroformate (1.2 mL, 12.55 mmol) and 4-dimethylaminopyridine (0.16 g, 1.31 mmol). The mixture is stirred at RT for 4 hours. The reaction is diluted with water and extracted with EtOAc, the organic phase is washed with saturated aqueous sodium chloride, dried over $Na_2SO_4$ and concentrated. The residue is purified by column chromatography on silica gel, eluting with DCM then DCM:MeOH (80:1) to afford the title compound (1.92 g, 80.5% yield). MS (m/z): 199 (M+H).

Preparation 106

1-(4-Fluorophenyl)-2-methylhydrazine

To a mixture of $LiAlH_4$ (1.1 g) in THF (15 mL) is added a solution of ethyl 2-(4-fluorophenyl)hydrazinecarboxylate (1.9 g, 9.59 mmol) in THF (10 mL) dropwise under nitrogen in an ice-salt bath. After the addition, the ice bath is removed and the mixture is heated to 60° C. overnight. The reaction is cooled and quenched with water. The precipitate is filtered and washed with EtOAc. The organic phase is separated, dried over $Na_2SO_4$, and concentrated. The residue is purified by flash chromatography, eluting with PE:EtOAc (80:1 to 60:1) to afford the title compound (1 g, 74% yield). MS (m/z): 141 (M+H).

Preparation 107

Ethyl 2-(4-fluorophenyl)-1,5-dimethyl-3-oxo-2,3-dihydro-1H-pyrazole-4-carboxylate A mixture of 1-(4-fluorophenyl)-2-methylhydrazine (0.6 g, 4.28 mmol), diethyl 2-acetylmalonate (0.96 g, 4.75 mmol), and acetic acid (0.51 g, 8.49 mmol) in water (15 mL) is heated at 115° C. for 3 hours. The reaction is cooled and extracted with EtOAc twice. The organic phase is washed with saturated aqueous sodium chloride, dried over $Na_2SO_4$ and concentrated. The residue is purified by column chromatography on silica gel, eluting with DCM:MeOH (from 150:1 to 60:1) to afford the title compound (0.59 g, 49.5% yield). MS (m/z): 279 (M+H).

Preparation 108

(E)-2-(2-(4-Fluorophenyl)hydrazono)acetaldehyde

A solution of 4-fluorophenylhydrazine hydrochloride (1 g, 6 mmol) in THF (20 mL) is treated with DIPEA (3 mL, 18 mmol). Then oxalaldehyde (40% in water, 0.89 g, 6.0 mmol) in THF (10 mL) is added dropwise in an ice-bath. After the addition, the mixture is stirred at RT for 30 min, quenched with water, and extracted with EtOAc. The organic phase is washed with saturated aqueous sodium chloride, dried over $Na_2SO_4$ and concentrated to afford the crude title compound (0.97 g, 97% yield). MS (m/z): 167 (M+H).

Preparation 109

Ethyl 2-(4-fluorophenyl)-3-oxo-2,3-dihydropyridazine-4-carboxylate

Crude (E)-2-(2-(4-fluorophenyl)hydrazono)acetaldehyde (0.97 g, 5.8 mmol) is dissolved in EtOH (50 mL), and diethyl malonate (0.93 g, 5.8 mmol) and piperidine (0.2 mL, 2.0 mmol) are added. The mixture is heated at reflux overnight. The reaction mixture is then cooled and concentrated. The residue is diluted with water and extracted with EtOAc twice. The combined organic extracts are dried over $Na_2SO_4$ and concentrated. The residue is purified by column chromatography on silica gel, eluting with PE:EtOAc (from 3:1 to 1:1), to afford title compound (0.26 g, 17% yield of two steps) MS (m/z): 263 (M+H).

Preparation 110

Methyl 3-(4-fluorophenylamino)-3-oxopropanoate

To a solution of 4-fluoroaniline (4.4 mL, 45 mmol) in acetone is added TEA (8.5 mL, 67 mmol) and methyl malonyl chloride (7.2 mL, 67 mmol). The mixture is stirred at RT for 5 hours and then concentrated. After water (20 mL) is added, the residue is acidified with concentrated HCl to pH 3. The precipitate is collected by filtration and washed with PE to give the product (14.1 g, 100% yield). MS (m/z): 212.1 (M+H).

The following compounds are prepared essentially by the method of Preparation 110:

| Prep. No. | Chemical name | Physical data MS (m/z) (M + H) |
|---|---|---|
| 111 | Ethyl 3-oxo-3-(phenylamino)propanoate | 208 |
| 112 | Ethyl 3-(4-fluorophenylamino)-3-oxopropanoate | 226.1 |

Preparation 113

Ethyl 1-(4-fluorophenyl)-6-methyl-2-oxo-1,2-dihydropyridine-3-carboxylate

To a solution of methyl 3-(4-fluorophenylamino)-3-oxopropanoate(10.1 g, 48 mmol) in EtOH (100 mL) is added trans-4-methoxy-3-buten-2-one (5.7 g, 57 mmol) and $CH_3ONa$ (3.1 g, 57 mmol). The mixture is heated at reflux overnight and then concentrated. The residue is purified by silica gel column chromatography eluting with PE:EtOAC (from 5:1 to 2:1) to give the product (2.1 g, 16% yield). MS (m/z): 276.1 (M+H).

The following compounds are prepared essentially by the method of Preparation 113:

| Prep. No. | Chemical name | Physical data MS (m/z) (M + H) |
|---|---|---|
| 114 | Ethyl 1-(4-fluorophenyl)-5-methyl-2-oxo-1,2-dihydropyridine-3-carboxylate | 276.1 |
| 115 | Ethyl 5-methyl-2-oxo-1-phenyl-1,2-dihydropyridine-3-carboxylate | 258.1 |

Preparation 116

(Z)-4-Aminopent-3-en-2-one

To a solution of 2,4-pentanedione (20.0 g, 0.2 mol) in water (20 mL) is added 25% aqueous ammonia (13.2 mL, 0.2 mol) dropwise at RT. The mixture is stirred at RT for 2 hours. Then the solvent is removed to give the product (20.0 g, 100% yield) as a solid. 1H NMR (Acetone-$d_6$, 300 MHz): 1.88 (s, 3H), 1.88 (s, 3H), 2.8 (br s, 1H), 6.54 (br s, 1H), 9.7 (brs, 1H).

Preparation 117

Ethyl 4,6-dimethyl-2-oxo-1,2-dihydropyridine-3-carboxylate

A solution of (Z)-4-aminopent-3-en-2-one (20.0 g, 0.2 mol) in dry THF (20 mL) is added to a solution of ethyl cyanoacetate (22.6 g, 0.2 mol) and TEA (20.2 g, 0.2 mol) in dry THF (200 mL). The reaction mixture is heated at reflux for 56 hours and then concentrated. The residue is kept standing at RT for 5 hours and the precipitate is filtered and washed with EtOAc to afford the title compound (7.3 g, 19.9% yield). MS (m/z): 196.0 (M+H).

Preparation 118

Ethyl 1-(4-fluorophenyl)-4,6-dimethyl-2-oxo-1,2-dihydropyridine-3-carboxylate

A suspension of ethyl 4,6-dimethyl-2-oxo-1,2-dihydropyridine-3-carboxylate (5.0 g, 0.025 mol), 4-fluorophenylboronic acid (10.7 g, 0.077 mol), cupric acetate (1.33 g, 0.007 mol), pyridine (6.86 mL), and 4 A molecular sieves (5.0 g) in 1,4-dioxane (80 mL) is heated at 80° C. for 68 hours. The solids are filtered off and the filtrate is concentrated. The residue is partitioned with EtOAc (50 mL) and 2N HCl (70 mL). The precipitated solid is collected by filtration and washed with EtOAc to give the title product (1.2 g). The EtOAc filtrate is separated, dried and concentrated. The residue is purified by silica gel column chromatography eluting with PE:EtOAc:MeOH (40:20:1) to give another portion of product (0.12 g), (1.32 g total, 17.8% yield). MS (m/z): 290.1 (M+H).

Preparation 119

Ethyl 4,6-dimethyl-2-oxo-1-phenyl-1,2-dihydropyridine-3-carboxylate

A suspension of ethyl 4,6-dimethyl-2-oxo-1,2-dihydropyridine-3-carboxylate (7.5 g, 0.038 mol), phenylboronic acid (14.1 g, 0.115 mol), cupric acetate (1.38 g, 0.008 mol), pyridine (7.5 mL) in 1,4-dioxane (80 mL) is heated at 80° C. for 96 hours. The solid is filtered off and the filtrate is concentrated. The residue is partitioned with EtOAc (50 mL) and 2N HCl (70 mL), and the precipitate is collected by filtration and washed with EtOAc to give the title product (2.95 g). The EtOAc solution is separated, dried and concentrated. The residue is purified by silica gel column chromatography eluting with PE:acetone (2:1) to give another portion of (0.3 g). (3.25 g, 31.2% yield). MS (m/z): 272.0 (M+H).

Preparation 120

Ethyl 5-(bromomethyl)-2-(4-fluorophenyl)-1-methyl-3-oxo-2,3-dihydro-1H-pyrazole-4-carboxylate To a solution of ethyl 2-(4-fluorophenyl)-1,5-dimethyl-3-oxo-2,3-dihydro-1H-pyrazole-4-carboxylate (1.2 g, 4.3 mmol) and azobisisobutyronitrile (AIBN) (0.09 g, 0.06 mmol) in DCM is added N-bromosuccinimide (NBS) (0.9 g, 4.3 mmol) in three portions at RT. The resulting reaction mixture is stirred at RT overnight. The mixture is concentrated and the residue is purified by silica gel column chromatography eluting with PE:EtOAc (4:1) to give the product as a white solid (1.3 g, 84% yield). MS (m/z) 357.0 (M+H).

Preparation 121

Ethyl 5-((1H-pyrazol-1-yl)methyl)-2-(4-fluorophenyl)-1-methyl-3-oxo-2,3-dihydro-1H-pyrazole-4-carboxylate To a solution of ethyl 5-(bromomethyl)-2-(4-fluorophenyl)-1-methyl-3-oxo-2,3-dihydro-1H-pyrazole-4-carboxylate (1.3 g, 3.6 mmol) and 1H-pyrazole (0.25 g, 3.6 mmol) in THF (50 mL) and $H_2O$ (1 mL) cooled in an ice-water bath is added solid KOH (0.2 g, 3.6 mmol) in three portions. After the reaction mixture is stirred at RT overnight, the solvent is removed. The residue is purified by silica gel column chromatography eluting with PE:EtOAc (4:1) to give the product (0.87 g, 70% yield). MS (m/z): 345.1 (M+H).

The following compounds are prepared essentially by the method of Preparation 121:

| Prep. No. | Chemical name | Physical data MS (m/z) (M + H) |
|---|---|---|
| 122 | Ethyl 2-(4-fluorophenyl)-1-methyl-5-(morpholinomethyl)-3-oxo-2,3-dihydro-1H-pyrazole-4-carboxylate | 364.1 |
| 123 | Ethyl 2-(4-fluorophenyl)-1-methyl-3-oxo-5-(piperidin-1-ylmethyl)-2,3-dihydro-1H-pyrazole-4-carboxylate | 362.1 |

Preparation 124

Ethyl 1-(4-fluorophenyl)-5-(morpholinomethyl)-2-oxo-1,2-dihydropyridine-3-carboxylate A mixture of ethyl 1-(4-fluorophenyl)-5-methyl-2-oxo-1,2-dihydropyridine-3-carboxylate (0.275 g, 1 mmol), NBS (0.2 g, 1.1 mmol), AIBN (40 mg, 0.2 mmol) in $CCl_4$ (20 mL) is heated at reflux for 3 hours. After the reaction is cooled down, morpholine (0.088 mL, 1 mmol) and $K_2CO_3$ (0.14 g, 1 mmol) are added. The reaction is stirred at RT for another 2 hours. The solvent is removed, and the residue is diluted with water (10 mL) and extracted with EtOAc (20 mL) twice. The combined organic phases are washed with saturated aqueous sodium chloride, dried, and concentrated. The residue is purified by silica gel column chromatography eluting with DCM:MeOH (from 100:1 to 50:1, containing 0.5% 2 N $NH_3$ in MeOH), to afford the title compound (0.17 g, 47% yield). MS (m/z): 361.1 (M+H).

Preparation 125

Ethyl 2-(4-fluorophenylcarbamoyl)-3-methylbut-2-enoate

To a solution of 4-fluoroaniline (2 g, 18 mmol) in diethyl isopropylidenemalonate (10 g, 50 mmol) is added 1H-imidazole (0.25 g, 3.67 mmol). The reaction mixture is stirred at 200° C. under $N_2$ for 3 hours. After the reaction is cooled, silica gel is added. The mixture is loaded onto a silica gel column, and eluted first with PE and then PE:EtOAc (3:1) to give the product (1.85 g, 39% yield). MS (m/z): 266.1 (M+H).

Preparation 126

Ethyl 1-(4-fluorophenyl)-4-methyl-2-oxo-1,2-dihydropyridine-3-carboxylate

A mixture of ethyl 2-(4-fluorophenylcarbamoyl)-3-methylbut-2-enoate (1.85 g, 6.97 mmol) and N,N-dimethylformamide dimethyl acetal (5 mL, 37.45 mmol) is stirred at 90° C. for 90 min. After the reaction is cooled, EtOAc (30 mL) and saturated $NH_4Cl$ solution (20 mL) are added. The organic phase is separated, dried and concentrated. The residue is purified by silica gel column chromatography eluting with DCM:MeOH (10:1). The fractions containing product are concentrated, and the residue is mixed with ether to give 1.2 g of yellow solid which is filtered and discarded. The filtrate is concentrated and purified again by silica gel column chromatography eluting with DCM:MeOH (20:1) to give the product (500 mg, 26% yield). MS (m/z): 276.1 (M+H).

Preparation 127

Ethyl 2-(4-fluorophenyl)-6-methyl-3-oxo-2,3-dihydropyridazine-4-carboxylate

To a suspension of 1-triphenylphosphoranylidene-2-propanone (3.18 g, 9.99 mmol) in THF (50 mL) is added diethyl ketomalonate (1.74 g, 9.99 mmol). The resulting mixture is stirred at RT for 30 min to give a clear solution. Then this solution is added to a solution of 4-fluorophenylhydrazine hydrochloride (1.62 g, 9.96 mmol) in EtOH:$H_2O$ (30 mL:30 mL). After the resulting mixture is refluxed for 1 hour, TEA (3 mL) is added and the mixture is stirred at reflux for another 1 hour. Then it is concentrated and the residue is partitioned with saturated aqueous $NH_4Cl$ (30 mL) and EtOAc (30 mL). The organic phase is separated, dried and concentrated. The residue is purified by silica gel column chromatography eluting with PE:EtOAc (3:1) to give the product (1.20 g, 43% yield). MS (m/z): 277.1 (M+H).

Preparation 128

1-(4-Fluorophenyl)-2-oxo-1,2-dihydropyridine-3-carboxylic acid

To a solution of methyl 1-(4-fluorophenyl)-2-oxo-1,2-dihydropyridine-3-carboxylate (10.0 g, 0.04 mol) in MeOH (150 mL) and water (50 mL) is added LiOH (1.9 g, 0.08 mol). The resulting reaction mixture is stirred at RT for 0.5 hour. After most of the MeOH is removed, the mixture is acidified with concentrated aqueous HCl until a white solid precipitates. The solid is collected by filtration and washed with water (5 mL) to give the desired product (8.7 g, 93% yield). MS (m/z): 234.0 (M+H).

The following compounds are prepared essentially by the method of Preparation 128:

| Prep. No. | Chemical name | Physical data MS (m/z) (M + H) |
|---|---|---|
| 129 | 2-(4-Fluorophenyl)-1,5-dimethyl-3-oxo-2,3-dihydro-1H-pyrazole-4-carboxylic acid | 251 |
| 130 | 2-(4-Fluomphenyl)-3-oxo-2,3-dihydropyridazine-4-carboxylic acid | 235 |
| 131 | 1-(4-Fluorophenyl)-6-methyl-2-oxo-1,2-dihydro-pyridine-3-carboxylic acid | 248.1 |
| 132 | 1-(4-Fluorophenyl)-4,6-dimethyl-2-oxo-1,2-dihydro-pyridine-3-carboxylic acid | |
| 133 | 4,6-Dimethyl-2-oxo-1-phenyl-1,2-dihydro-pyridine-3-carboxylic acid | 244.0 |
| 134* | 5-((1H-Pyrazol-1-yl)methy1)-2-(4-fluorophenyl)-1-methyl-3-oxo-2,3-dihydro-1H-pyrazole-4-carboxylic acid | |
| 135** | 2-(4-Fluorophenyl)-1-methyl-5-(morpholinomethyl)-3-oxo-2,3- dihydro-1H-pyrazole-4-carboxylic acid | 336.1 |
| 136 | 2-(4-Fluorophenyl)-1-methyl-3-oxo-5-(piperidin-1-ylmethyl)-2,3-dihydro-1H-pyrazole-4-carboxylic acid | 334.1 |
| 137 | 1-(4-Fluorophenyl)-5-methyl-2-oxo-1,2-dihydro-pyridine-3-carboxylic acid | 248.0 |
| 138 | 5-Methyl-2-oxo-l-phenyl-1,2-dihydropyridine-3-carboxylic acid | 230.1 |
| 139 | 1-(4-Fluorophenyl)-5-(morpholinomethyl)-2-oxo-1,2-dihydropyridine-3-carboxylic acid | 333.1 |

-continued

| Prep. No. | Chemical name | Physical data MS (m/z) (M + H) |
|---|---|---|
| 140** | 1-(4-Fluorophenyl)-4-methyl-2-oxo-1,2-dihydropyridine-3-carboxylic acid | 248.1 |
| 141 | 2-(4-Fluorophenyl)-6-methyl-3-oxo-2,3-dihydropyridazine-4-carboxylic acid | 249.0 |

*KOH is used as the base.
**NaOH is used as the base.

Preparation 142

6-Methyl-2-oxo-1-phenyl-1,2-dihydro-pyridine-3-carboxylic acid

To a solution of sodium ethoxide in EtOH (prepared from sodium (0.5 g, 21.75 mmol) dissolved in EtOH (40 mL)) is added ethyl 3-oxo-3-(phenylamino)propanoate (4 g, 19.30 mmol) and trans-4-methoxy-3-buten-2-one (2 g, 19.98 mmol). After the reaction is stirred at reflux overnight, the mixture is concentrated. The residue is partitioned between $H_2O$ (50 mL) and EtOAc (50 mL). The aqueous layer is acidified with concentrated HCl to a pH 3~4 and then it is extracted with EtOAc. The organic extracts are dried and concentrated. The residue is purified by silica gel column chromatography eluting with DCM:MeOH (25:1) to give the product (1.20 g, 27% yield). MS (m/z): 230.0 (M+H).

Preparation 143

1,5-Dimethyl-3-oxo-2-phenyl-2,3-dihydro-1H-pyrazole-4-carboxylic acid

To a mixture of 1,5-dimethyl-3-oxo-2-phenyl-2,3-dihydro-1H-pyrazole-4-carbaldehyde (2 g, 9.25 mmol) in water (100 mL) at 75° C. is added a solution of $KMnO_4$ (1.5 g, 9.49 mmol) in water (200 mL) slowly. After the addition is complete, the reaction mixture is stirred at 75° C. for another 1 hour. Solid KOH is added to make the solution alkaline and the mixture is filtered while it is hot. To the filtrate is added EtOH (10 mL) and EtOAc (50 mL). The organic phase is separated and discarded. The aqueous phase is acidified with concentrated HCl to pH 5 and extracted with EtOAc (60 mL) and DCM (60 mL). The organic phases are combined, dried, and concentrated to give the title product (1.9 g, 88.46%yield). MS (m/z): 233.1 (M+H).

Preparation 144

Ethyl 3-(4-fluorophenylamino)-3-oxopropanoate

To a 4-necked 10 L round bottom flask, is added DCM (5000 mL), 4-fluoroaniline (111 g, 1.0 mol) and TEA (166 mL, 1.2 mol). Ethyl malonyl chloride (196 g, 1.3 mol) in DCM (500 mL) is added dropwise under $N_2$ at 0-5° C. (under ice bath) during 4 hours. After addition, the mixture is stirred for 30 min at this temperature. Water (2 L) is added into the mixture with stirring at this temperature. The organic phase is washed with saturated $NaHCO_3$, saturated aqueous sodium chloride and dried over anhydrous $Na_2SO_4$. The aqueous phase is extracted with EtOAc (2×1 L). The organic phase is washed with saturated aqueous sodium chloride and dried over anhydrous $Na_2SO_4$. After filtration, the residue is washed with PE (1 L) to give ethyl 3-(4-fluorophenylamino)-3-oxopropanoate (230 g, crude yield 102%) as a yellow solid. MS (m/z): 226.1 (M+H).

Preparation 145

1-(4-Fluorophenyl)-6-methyl-2-oxo-1,2-dihydropyridine-3-carboxylic acid

To a 4-necked 3 L round bottom flask, is added EtOH (1500 mL), ethyl 3-(4-fluorophenylamino)-3-oxopropanoate (139 g, 617 mmol), sodium ethoxide (65.6 g, 925 mmol) and 4-methoxy-3-buten-2-one (103 g, 925 mmol). The mixture is refluxed for 3 hours. After the solution is cooled to RT, the reaction mixture is concentrated under reduced pressure to remove the EtOH. The residue is diluted with DCM (700 mL) and 1 M HCl (1500 mL). The aqueous phase is extracted with DCM (3×500 mL). The combined organic extracts are washed with saturated aqueous sodium chloride (1000 mL), dried over anhydrous $Na_2SO_4$ and concentrated under reduced pressure. The residue is triturated with EtOAc (150 mL) at RT (10-15° C.) for 1 hour. After filtration and washing with EtOAc (50 mL), 1-(4-fluorophenyl)-6-methyl-2-oxo-1,2-dihydropyridine-3-carboxylic acid is obtained as a yellow solid (85.3 g, 56% yield). MS (m/z): 248 (M+H).

Example 1

N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide

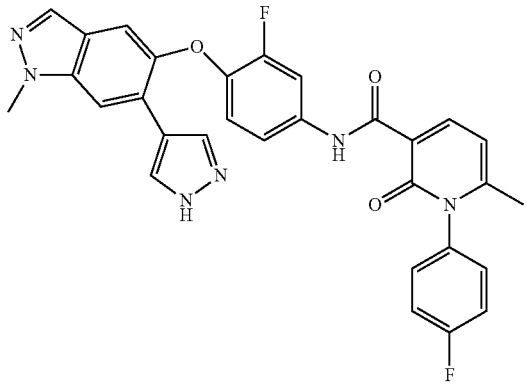

To a 100 mL round bottom flask is added tert-butyl 4-(5-(4-amino-2-fluorophenoxy)-1-methyl-1H-indazol-6-yl)-1H-pyrazole-1-carboxylate (1.43 g, 3.38 mmol), 1-(4-flurorophenyl)-6-methyl-2-oxo-1,2-dihydropyridine-3-carboxylic acid (1.25 g, 5.07 mmol), EDCI (1.48 g, 7.6 mmol) and HOBt (776 mg, 5.07 mmol) followed by DMF (15 mL, 193.99 mmol) and then DIPEA (1.47 mL, 8.44 mmol). The mixture is allowed to stir at RT overnight. The reaction mixture is diluted into EtOAc (300 mL) and washed with saturated aqueous sodium chloride (5×100 mL). The combined aqueous solution is extracted with EtOAc (1×100 mL) and then the combined organic solutions are dried over $N_2SO_4$, filtered, and concentrated to dryness. The solid is purified on a silica gel column eluting with DCM (A) and a 10% MeOH in a DCM solution (B), gradient from 100% (A) to 80% (A):20% (B) over 70 min to give tert-butyl 4-(5-(2-fluoro-4-(1-(4-fluorophenyl)-6-methyl-2-oxo-1,2-dihydropyridine-3-carboxamido)phenoxy)-1-methyl-1H-indazol-6-yl)-1H-pyrazole-1-carboxylate as a gold solid (2.20 g, 87% yield). MS (m/z): 653. (M+H), 675 (M+Na).

To a round bottom flask is added tert-butyl 4-(5-(2-fluoro-4-(1-(4-fluorophenyl)-6-methyl-2-oxo-1,2-dihydropyridine-3-carboxamido)phenoxy)-1-methyl-1H-indazol-6-yl)-1H-pyrazole-1-carboxylate (1.92 g, 2.94 mmol) and DCM (50 mL) followed by triethylsilane (1.88 mL, 11.77 mmol) and TFA (17.8 mL, 235.35 mmol). The reaction mixture is allowed to stir at RT for 1.5 hours. The solvent is removed and diluted into DCM (150 mL) and washed with saturated aqueous $NaHCO_3$ solution (2×100 mL). The organic solution is dried with $Na_2SO_4$, and concentrated under reduced pressure to give a solid material. The solid is purified on a silica gel column eluting with DCM (A) and a 10% MeOH in DCM solution (B), gradient from 100% (A) to 75%(A):25%(B) over 70 min, held at this 75:25 ratio for 15 min to give the title compound as an off-white solid. The solid is dissolved in hot EtOH (50 mL) followed by a portion-wise addition of distilled water (250 mL) causing a white solid to precipitate. The solid is filtered over a Buchner funnel and washed with distilled water (3×15 mL), air dried, and vacuum dried at 60° C. for 15 hours to give the title compound as an off-white solid (1.27 g, 78% yield). MS (m/z): 552.8 (M+H).

Example 2

N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide

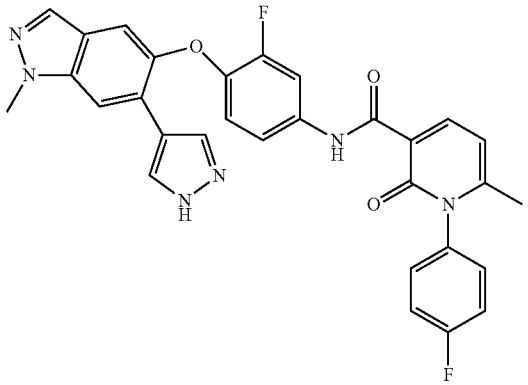

A 12 L round bottom flask is equipped with overhead agitation, a thermocouple, and a $N_2$ purge. tert-Butyl 4-(5-(4-amino-2-fluorophenoxy)-1-methyl-1H-indazol-6-yl)-1H-pyrazole-1-carboxylate (404 g, 954.08 mmol) is dissolved in DMF (2 L) and charged to the flask. DMF (1 L) is used to rinse the flask. 1-(4-Fluorophenyl)-6-methyl-2-oxo-1,2-dihydropyridine-3-carboxylic acid (259.46 g, 1.05 mol) and EDCI (228.63 g, 1.19 mol) are added and it is rinse in with DMF (500 mL). Then HOBt (189.94 g, 1.24 mol) is added and it is again rinsed in with DMF (500 mL). Finally, DIPEA is slowly added (184.97 g, 1.43 mol). The dark solution is then stirred at RT over the weekend. To a 20 L bottom outlet flask is added DI water (3 L) and DCM (5 L). The reaction mixture is poured in and it is rinsed in with DCM (1 L). The organic layer is separated, washed with DI water (3×3 L), dried over $Na_2SO_4$, filtered, rinsed solids with DCM and concentrated the filtrate. EtOAc (2 L) is added to the residue and the solution is stirred for 1 hour. The product crystallizes out. The mixture is concentrated. Another portion of EtOAc (2 L) is added and concentrated to remove all of the DCM. EtOAc (650 mL) and MTBE (3 L) are added to the residue and the solution is stirred in an ice bath for 1 hour. The tan slurry is filtered using a polypropylene pad. The cake is rinsed with MTBE (2×500 mL). The light tan solid is dried overnight in the vacuum oven at 40° C. to give the crude product (553 g). The crude product is purified by silica gel column chromatography eluting with (50% EtOAc (50%):35% DCM (35%): n-heptane (15%)) to give the pure desired product tert-butyl 4-(5-(2-fluoro-4-(1-(4-fluorophenyl)-6-methyl-2-oxo-1,2-dihydropyridine-3-carboxamido)phenoxy)-1-methyl-1H-indazol-6-yl)-1H-pyrazole-1-carboxylate (424 g, 68%). MS (m/z): 651.0 (M−H).

tert-Butyl 4-(5-(2-fluoro-4-(1-(4-fluorophenyl)-6-methyl-2-oxo-1,2-dihydropyridine-3-carboxamido)phenoxy)-1-methyl-1H-indazol-6-yl)-1H-pyrazole-1-carboxylate (423.9 g, 649.50 mmol) is dissolved in DCM (4.24 L). HCl in MeOH (5.74 N, 799.99 mL, 4.59 mol) is added and the solution is heated at 30° C. for 1 hour. Then the reaction mixture is heated to 45° C. and DCM (1.5 L) is added. After two hours, the solution is heated to 50° C. and DCM (2 L) is added. After 3 hours, DCM (2 L) is added followed by HCl in MeOH (4.5 N, 721.67 mL, 3.25 mol). After another 45 min, DCM (1 L), HCl in MeOH (4.5 N, 288.67 mL, 1.30 mol), and MeOH (1.5 L) are added. The reaction solution is then heated to 60° C. After 4 hours, MeOH (2 L) is added and 10 min later DCM (1 L) is added followed by HCl in MeOH (4.5 N, 200 mL). After 5 hours, the reaction is complete. The reaction mixture is concentrated to about ⅓ volume. MeOH (2 L) is added and the solution is concentrated to a thick slurry. Again, MeOH (2 L) is added and the mixture is concentrated to a thick slurry. The slurry is cooled to about 10-15° C. and then filtered. The solids are washed with MeOH. The solids are placed in a 55° C. vacuum oven for 2 days to give the desired product N-(3-fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide hydrochloride (377 g, 92.8%). MS (m/z): 551.0 (M−H).

To a 22 L round bottom flask equipped with mechanical stirring under nitrogen is added N-(3-fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide hydrochloride (367 g, 0.62 mol) followed by DCM (7.34 L) and water (7.34 L). $Na_2CO_3$ (181.6 g, 1.71 mol) is added and the mixture is stirred at RT for 30 min. The pH is checked and found to be about 9.4. The mixture is filtered over polypropylene. The solids are collected and placed into a 5 L round bottom flask. A 20% water/MeOH solution (2.6 L) is added and the slurry is stirred for 30 min. The slurry is filtered and the solids are washed with 20% water/MeOH (600 mL). The solids are placed in a vacuum oven at 35° C. overnight. The first weighing indicates 394 g (theoretical yield 324.8 g, about 121% mass recovery). TGA (Thermogravimetric analysis)/DSC (differential scanning calorimetry) shows about 17 wt % free water and 10-11 wt% volatile loss at the melt. The solids are dried at 55° C. in a vacuum oven with a $N_2$ sweep for 3.5 hours (354.7 g, about 109% mass recovery, NMR shows about 9.3 wt % DCM). No free water is present according to TGA/DSC. The material is sent for milling.

The jet mill (Aljet™ 0101) in a glove bag is assembled inside a walk in hood and hooked up to $N_2$ to a 100 lb header. The inlet pusher nozzle is adjusted for maximum draw and max nitrogen flow is introduced into the mill. Pressure readings are noted as 90 psi on pusher nozzle and 85 psi on both grind nozzles. The starting material (353.4 g) is slowly fed to the mill inlet, stopping to empty the receiver sock as needed. The total milling time is 22 min and 25 second. The calculated feed rate is 15.8 g/min (353.4 grams divided by 22.42 min). The milled material (335.7 g, 95%) is obtained with 17.7 g loss. Particle size analysis result of the milled material is d90 of 4.6 microns.

TGA/DSC indicates about 11.4 wt % volatiles at the melt and NMR (DMSO) shows about 9.3 wt % DCM. $^1$H NMR (DMSO) δ 12.94 (br s, 1 H), 11.88 (s, 1H), 8.44 (d,J=7.47 Hz, 1 H), 8.12 (br s, 1 H), 8.00 (br s, 1 H), 7.96 (s, 1 H), 7.94 (d,J=2.2 Hz, 1 H), 7.91 (d,J=2.6 Hz, 1 H), 7.87 (s, 1H), 7.47-7.37 (m, 5 H), 6.82 (t,J=9.26 Hz, 8.82 Hz, 1 H), 6.65 (d,J=7.49 Hz, 1 H), 4.04 (s, 3 H), 2.03 (s, 3 H). LC/MS: (M+H) 553.1.

Anhydrous Crystal Form Preparation

To 10 mL of EtOH is added 120 mg of the above compound into a 20 mL vial. The sample is heated to 70° C. with stirring. Initially the solids start to dissolve and then a suspension forms followed by a white precipitate. The sample is cooled to RT while being stirred. A small sample of the slurry is taken by pipette and allowed to air dry. This material is highly crystalline and proves to be an ethanol solvate by TGA. To the remaining suspension, 10 mL of heptane is added and then heated to boiling. The measured temperature is monitored at 70.8° C. until the volume has been reduced to 10 mL. When the temperature starts to rise, the heat is removed and the slurry stirred at RT overnight. The solid is isolated by vacuum filtration and dried in a vacuum oven at 45° C. for 3 hours, resulting in 77% recovery. The crystalline form shows a weight loss of 0.17% from 25-238° C. by TGA. The form's onset of melting is 247.8° C.

Example 3

N-(3-Fluoro-4-(1-methyl-6-(1H-pyrazol-4-yl)-1H-indazol-5-yloxy)phenyl)-1-(4-fluorophenyl)-4,6-dimethyl-2-oxo-1,2-dihydropyridine-3-carboxamide methanesulfonate

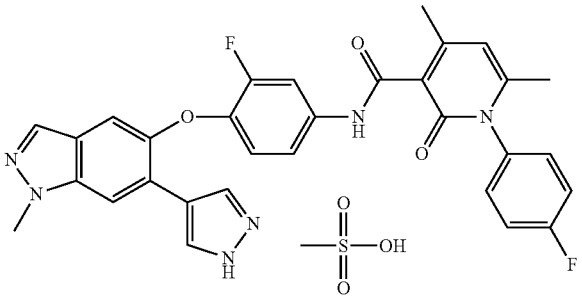

To a solution of 3-fluoro-4-(1-methyl-6-(1H-pyrazol-4-yl)-1H-indazol-5-yloxy)aniline (300 mg, 927.8 μmol) and 1-(4-fluorophenyl)-4,6-dimethyl-2-oxo-1,2-dihydropyridine-3-carboxylic acid (300 mg, 1. 15 mmol) in DMF (5 mL) is added HOBt (130 mg, 0.962 mmol), EDCI (180 mg, 0.939 mmol) and N-methylmorpholine (0.5 mL). After the reaction mixture is stirred at 60° C. overnight, it is partitioned between EtOAc (50 mL) and saturated aqueous $NH_4Cl$ (30 mL). The organic phase is separated, dried and concentrated. The residue is triturated with EtOAc (5 mL) and the solids are collected by filtration to give N-(3-fluoro-4-(1-methyl-6-(1H-pyrazol-4-yl)-1H-indazol-5-yloxy)phenyl)-1-(4-fluorophenyl)-4,6-dimethyl-2-oxo-1,2-dihydropyridine-3-carboxamide as the desired product (230 mg, 43.7% yield.) MS (m/z): 567.2 (M+H).

To a solution of N-(3-fluoro-4-(1-methyl-6-(1H-pyrazol-4-yl)-1H-indazol-5-yloxy)phenyl)-1-(4-fluorophenyl)-4,6-dimethyl-2-oxo-1,2-dihydropyridine-3-carboxamide (230 mg, 0.406 mmol) in acetone (10 mL) is added $MeSO_3H$ (39 mg, 0.406 mmol). After the reaction is stirred at RT for 0.5 hour, it is concentrated. The residue is washed with ether and dried to give N-(3-fluoro-4-(1-methyl-6-(1H-pyrazol-4-yl)-1H-indazol-5-yloxy)phenyl)-1-(4-fluorophenyl)-4,6-dimethyl-2-oxo-1,2-dihydropyridine-3-carboxamide methanesulfonate (250 mg, 92.9% yield.) MS (m/z): 567.2 (M+H). The following compounds are prepared essentially by the method of Example 3 with the exception that in certain cases the freebase is generated and not the salt:

| Ex. No. | Chemical name | Structure | Physical data MS (m/z) (M + H) |
|---|---|---|---|
| 4 | 1-(4-Fluorophenyl)-6-methyl-N-(4-(1-methyl-6-(1H-pyrazol-4-yl)-1H-indazol-5-yloxy)phenyl)-2-pxp-1,2-dihydropyridine-3-carboxamide methanesulfonate | 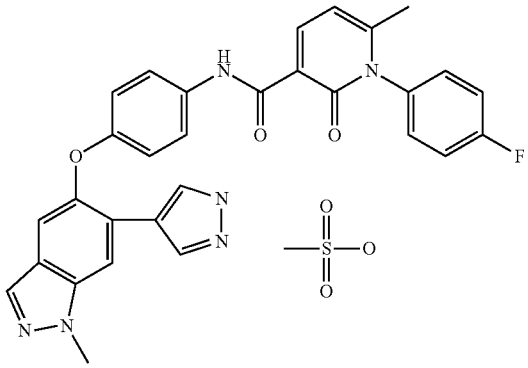 | 535.2 |

-continued

| Ex. No. | Chemical name | Structure | Physical data MS (m/z) (M + H) |
|---|---|---|---|
| 5 | N-(3-Fluoro-4-(1-methyl-6-(1H-pyrazol-4-yl)-1H-indazol-5-yloxy)phenyl)-6-methyl-2-oxo-1-phenyl-1,2-dihydropyridine-3-carboxamide methanesulfonate | | 535.1 |
| 6 | N-(3-Fluoro-4-(1-methyl-6-(1H-pyrazol-4-yl)-1H-indazol-5-yloxy)phenyl)-4,6-dimethyl-2-oxo-1-phenyl-1,2-dihydropyridine-3-carboxamide methanesulfonate | | 549.1 |
| 7 | N-(3-Fluoro-4-(1-methyl-6-(1H-pyrazol-4-yl)-1H-indazol-5-yloxy)phenyl)-2-(4-fluorophenyl)-1,5-dimethyl-3-oxo-2,3-dihydro-1H-pyrazole-4-carboxamide methanesulfonate | | 556.2 |
| 8 | N-(3-Fluoro-4-(1-methyl-6-(1H-pyrazol-4-yl)-1H-indazol-5-yloxy)phenyl)-2-(4-fluorophenyl)-3-oxo-2,3-dihydropyridazine-4-carboxamide methanesulfonate | | 540.2 |

-continued

| Ex. No. | Chemical name | Structure | Physical data MS (m/z) (M + H) |
|---|---|---|---|
| 9 | N-(3-Fluoro-4-(1-methyl-6-(2-methylpyridin-4-yl)-1H-indazol-5-yloxy)phenyl)-1-(4-fluorophenyl)-6-methyl-2-oxo-1,2-dihydropyridine-3-carboxamide methanesulfonate | 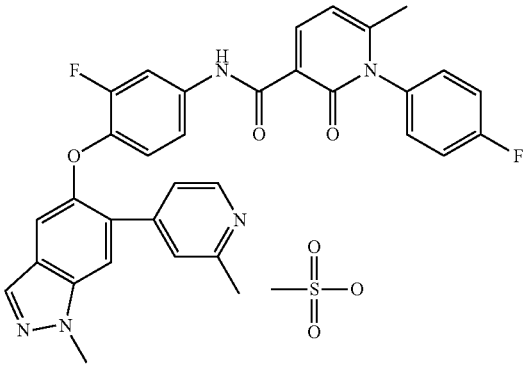 | 578.1 |
| 10 | 6-Methyl-N-(4-(1-methyl-6-(1H-pyrazol-4-yl)-1H-indazol-5-yloxy)phenyl)-2-oxo-1-phenyl-1,2-dihydropyridine-3-carboxamide methanesulfonate | 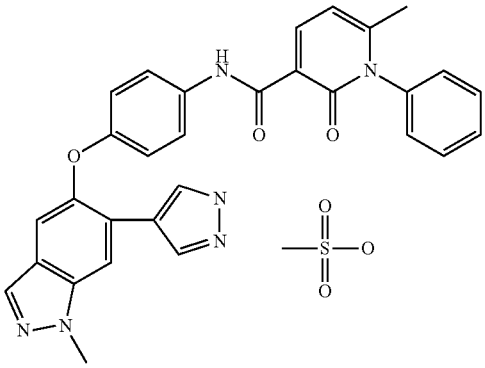 | 517.2 |
| 11 | 5-((1H-Pyrazol-1-yl)methyl)-N-(3-fluoro-4-(6-morpholino-1H-indazol-5-yloxy)phenyl)-2-(4-fluorophenyl)-1-methyl-3-oxo-2,3-dihydro-1H-pyrazole-4-carboxamide | 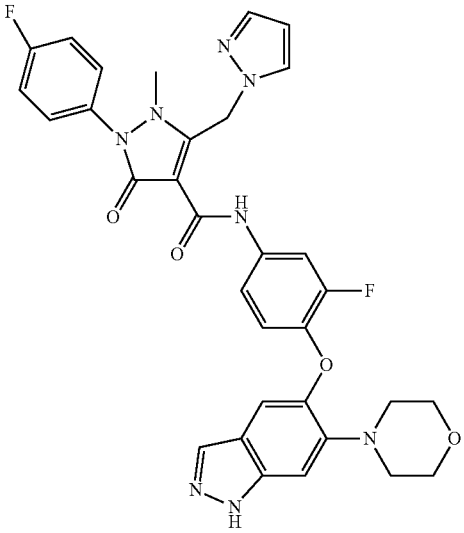 | 627.2 |

-continued

| Ex. No. | Chemical name | Structure | Physical data MS (m/z) (M + H) |
|---|---|---|---|
| 12 | N-(3-Fluoro-4-(6-morpholino-1H-indazol-5-yloxy)phenyl)-1-(4-fluorophenyl)-6-methyl-2-oxo-1,2-dihydropyridine-3-carboxamide | 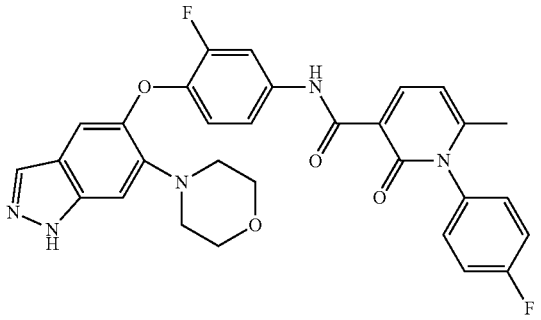 | 558.1 |
| 13 | N-(4-(6-(Dimethylamino)-indazol-5-yloxy)-3-fluorophenyl)-6-methyl-2-oxo-1-phenyl-1,2-dihydropyridine-3-carboxamide methanesulfonate | 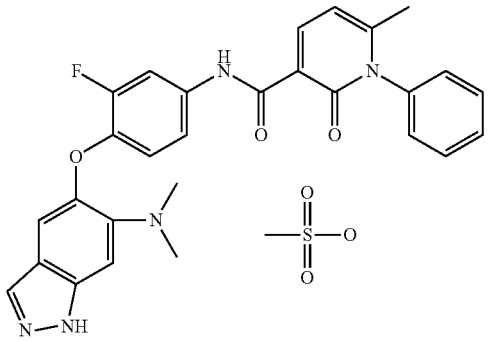 | 498.2 |
| 14 | N-(3-Fluoro-4-(1-methyl-6-(1H-pyrazol-4-yl)-1H-indazol-5-yloxy)phenyl)-1-(4-fluorophenyl)-5-methyl-2-oxo-1,2-dihydropyridine-3-carboxamide methanesulfonate | 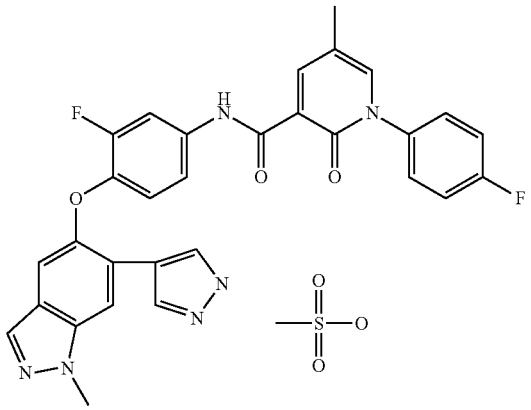 | 553.1 |
| 15 | N-(3-Fluoro-4-(6-(pyridin-3-yl)-1H-indazol-5-yloxy)phenyl)-1-(4-fluorophenyl)-6-methyl-2-oxo-1,2-dihydropyridine-3-carboxamide | 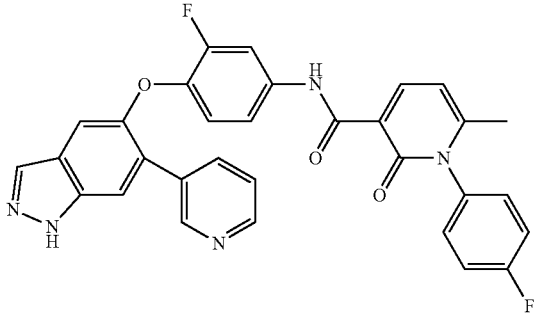 | 550.2 |

-continued

| Ex. No. | Chemical name | Structure | Physical data MS (m/z) (M + H) |
|---|---|---|---|
| 16 | 5-((1H-Pyrazol-1-yl)methyl)-N-(4-(6-(dimethylamino)-1H-indazol-5-yloxy)-3-fluorophenyl)-2-(4-fluorophenyl)-1-methyl-3-oxo-2,3-dihydro-1H-pyrazole-4-carboxamide methanesulfonate | | 585.1 |
| 17 | l-(4-Fluorophenyl)-4,6-dimethyl-N-(4-(1-methyl-6-(1H-pyrazol-4-yl)-1H-indazol-5-yloxy)phenyl)-2-oxo-1,2-dihydropyridine-3-carboxamide methanesulfonate | | 549.2 |
| 18 | N-(3-Fluoro-4-(6-morpholino-1H-indazol-5-yloxy)phenyl)-1-(4-fluorophenyl)-2-oxo-1,2-dihydropyridine-3-carboxamide methanesulfonate | | 544.2 |
| 19 | N-(3-Fluoro-4-(6-(tetrahydro-2H-pyran-4-ylamino)-1H-indazol-5-yloxy)phenyl)-1-(4-fluorophenyl)-4,6-dimethyl-2-oxo-1,2-dihydropyridine-3-carboxamide methanesulfonate | | 586.1 |

-continued

| Ex. No. | Chemical name | Structure | Physical data MS (m/z) (M + H) |
|---|---|---|---|
| 20 | N-(4-(6-(Dimethylamino)-1H-indazol-5-yloxy)-3-fluorophenyl)-2-(4-fluorophenyl)-3-oxo-2,3-dihydropyridazine-4-carboxamide | 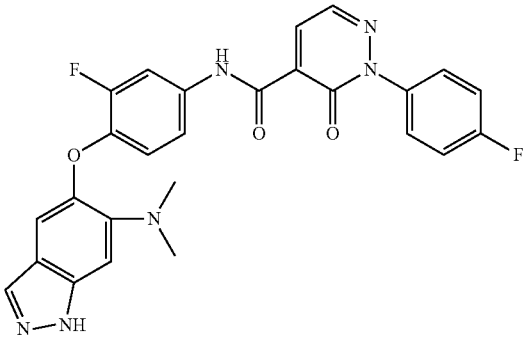 | 503.1 |
| 21 | N-(4-(6-(Dimethylamino)-1H-indazol-5-yloxy)-3-fluorophenyl)-1-(4-fluorophenyl)-4,6-dimethyl-2-oxo-1,2-dihydropyridine-3-carboxamide | 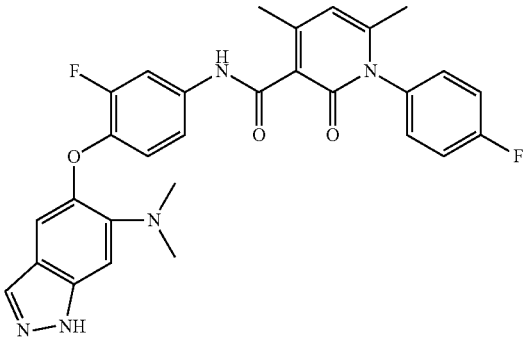 | 530.2 |
| 22 | N-(4-(6-(Dimethylamino)-1H-indazol-5-yloxy)phenyl)-6-methyl-2-oxo-1-phenyl-1,2-dihydropyridine-3-carboxamide methanesulfonate | 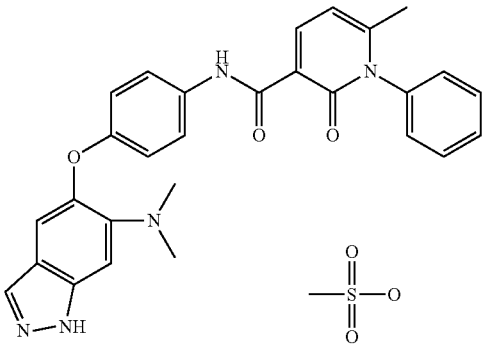 | 480.2 |
| 23 | N-(3-Fluoro-4-(6-(6-methylpyridin-3-yl)-1H-indazol-5-yloxy)phenyl)-1-(4-fluorophenyl)-6-methyl-2-oxo-1,2-dihydropyridine-3-carboxamide | 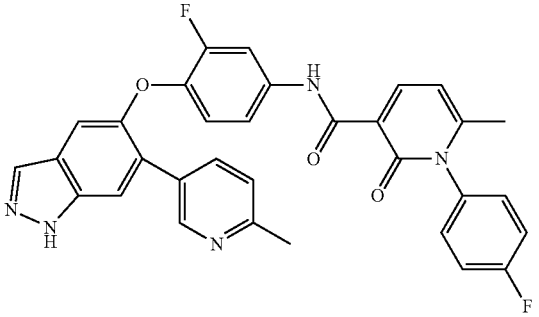 | 564.1 |

-continued

| Ex. No. | Chemical name | Structure | Physical data MS (m/z) (M + H) |
|---|---|---|---|
| 24 | 4,6-Dimethyl-N-(4-(1-methyl-6-(1H-pyrazol-4-yl)-1H-indazol-5-yloxy)phenyl)-2-oxo-1-phenyl-1,2-dihydropyridine-3-carboxamide methanesulfonate | 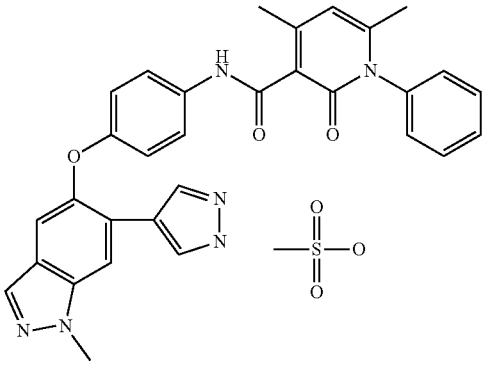 | 531.2 |
| 25 | N-(3-Fluoro-4-(1-methyl-6-(pyridin-3-yl)-1H-indazol-5-yloxy)phenyl)-2-(4-fluorophenyl)-1,5-dimethyl-3-oxo-2,3-dihydro-1H-pyrazole-4-carboxamide methanesulfonate | 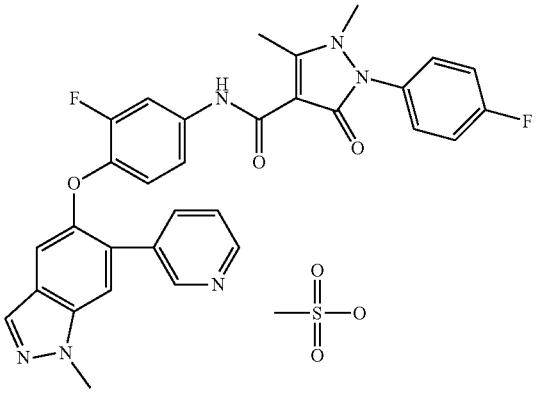 | 567.1 |
| 26 | N-(3-Fluoro-4-(6-morpholino-1H-indazol-5-yloxy)phenyl)-1-(4-fluorophenyl)-2-oxo-1,2-dihydropyridine-3-carboxamide | 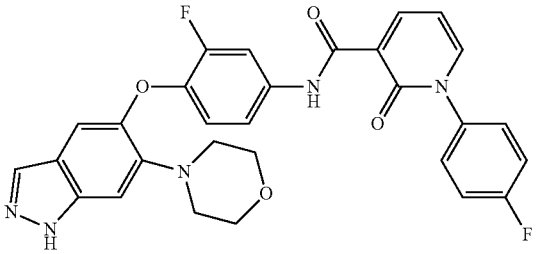 | 544.1 |
| 27 | 5-Methyl-N-(4-(1-methyl-6-(1H-pyrazol-4-yl)-1H-indazol-5-yloxy)phenyl)-2-oxo-1-phenyl-1,2-dihydropyridine-3-carboxamide methanesulfonate | 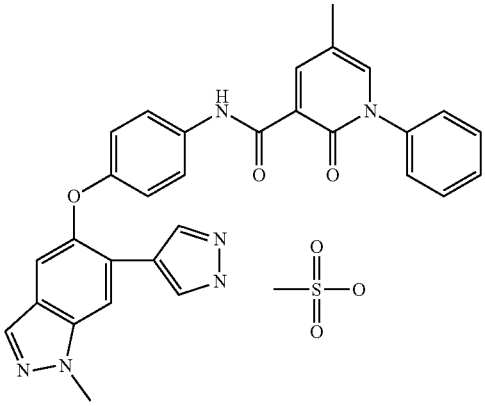 | 517.1 |

-continued

| Ex. No. | Chemical name | Structure | Physical data MS (m/z) (M + H) |
|---|---|---|---|
| 28 | N-(3-Fluoro-4-(6-morpholino-1H-indazol-5-yloxy)phenyl)-2-(4-fluorophenyl)-1-methyl-5-(morpholinomethyl)-3-oxo-2,3-dihydro-1H-pyrazole-4-carboxamide methanesulfonate | 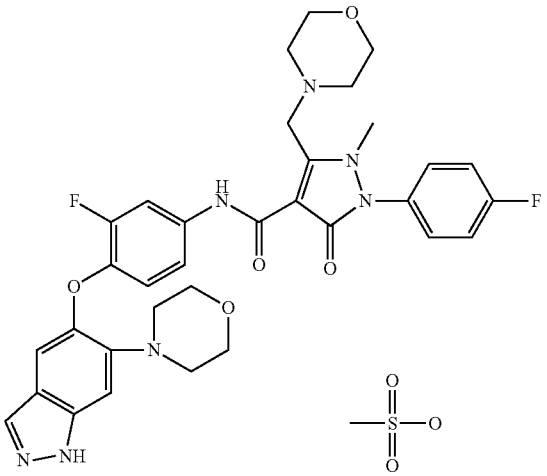 | 646.2 |
| 29 | N-(3-Fluoro-4-(6-(pyridin-3-yl)-1H-indazol-5-yloxy)phenyl)-1-(4-fluorophenyl)-2-oxo-1,2-dihydropyridine-3-carboxamide | 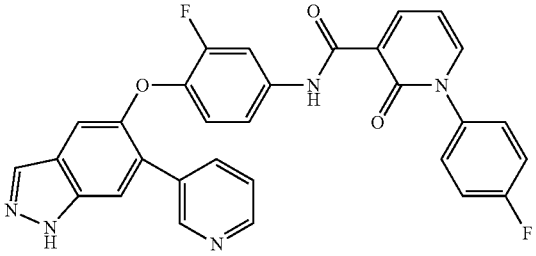 | 535.5 |
| 30 | N-(3-Fluoro-4-(6-(pyridin-3-yl)-1H-indazol-5-yloxy)phenyl)-2-(4-fluorophenyl)-1-methyl-5-(morpholinomethyl)-3-oxo-2,3-dihydro-1H-pyrazole-4-carboxamide | 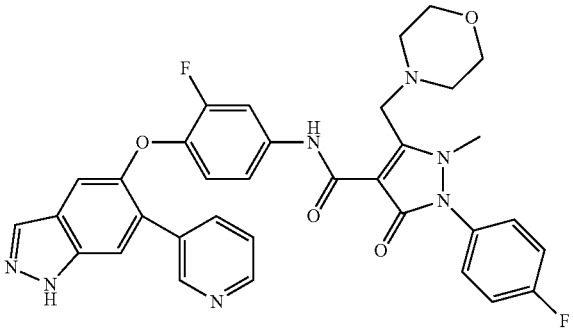 | 638.2 |
| 31 | N-(3-Fluoro-4-(6-(pyridin-4-yl)-1H-indazol-5-yloxy)phenyl)-2-(4-fluorophenyl)-3-oxo-2,3-dihydropyridazine-4-carboxamide methanesulfonate | 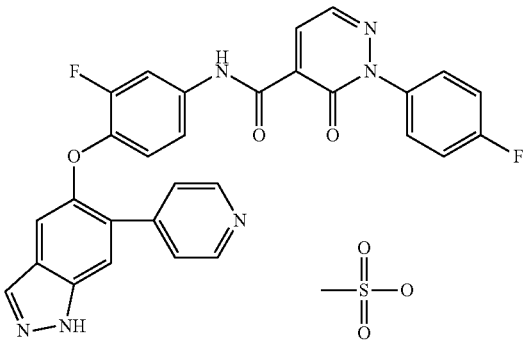 | 537.1 |

-continued

| Ex. No. | Chemical name | Structure | Physical data MS (m/z) (M + H) |
|---|---|---|---|
| 32 | N-(3-Fluoro-4-(6-(pyridin-4-yl)-1H-indazol-5-yloxy)phenyl)-2-(4-fluorophenyl)-1,5-dimethyl-3-oxo-2,3-dihydro-1H-pyrazole-4-carboxamide methanesulfonate | 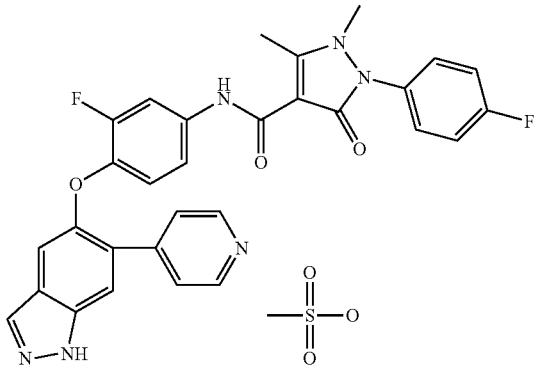 | 553.2 |
| 33 | N-(3-Fluoro-4-(6-(pyridin-3-yl)-1H-indazol-5-yloxy)phenyl)-2-(4-fluorophenyl)-1,5-dimethyl-3-oxo-2,3-dihydro-1H-pyrazole-4-carboxamide methanesulfonate | 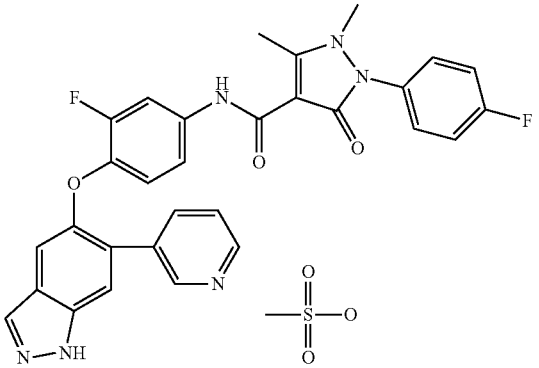 | 553.1 |
| 34 | N-(4-(6-(1H-Pyrazol-4-yl)-1H-indazol-5-yloxy)-3-fluorophenyl)-2-(4-fluorophenyl)-6-methyl-3-oxo-2,3-dihydropyridazine-4-carboxamide methanesulfonate | 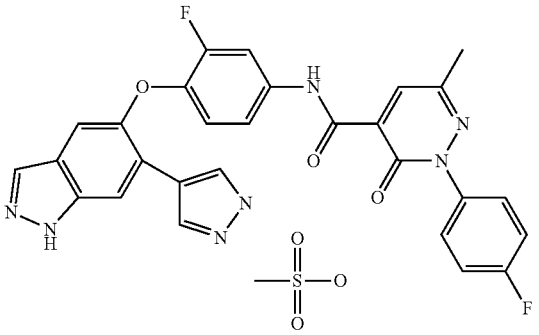 | 540.1 |
| 35 | N-(4-(6-Dimethylamino)-1H-indazol-5-yloxy)-3-fluorophenyl)-1-(4-fluorophenyl)-6-methyl-2-oxo-1,2-dihydropyridine-3-carboxamide | 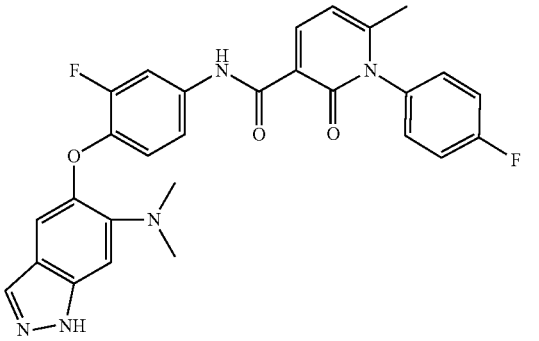 | 516.2 |

-continued

| Ex. No. | Chemical name | Structure | Physical data MS (m/z) (M + H) |
|---|---|---|---|
| 36 | N-(3-Fluoro-4-(6-morpholino-1H-indazol-5-yloxy(phenyl)-1-(4-fluorophenyl)-5-(morpholinomethyl)-2-oxo-1,2-dihydropyridine-3-carboxamide | 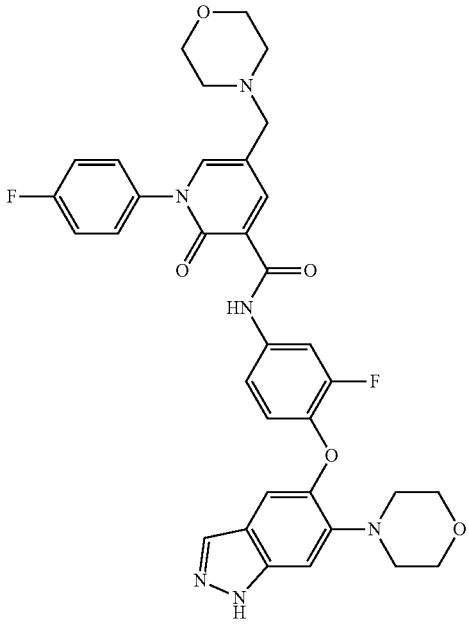 | 643.2 |
| 37 | N-(3-Fluoro-4-(6-morpholino-1H-indazol-5-yloxy)phenyl)-1-(4-fluorophenyl)-4-methyl-2-oxo-1,2-dihydropyridine-3-carboxamide methanesulfonate | 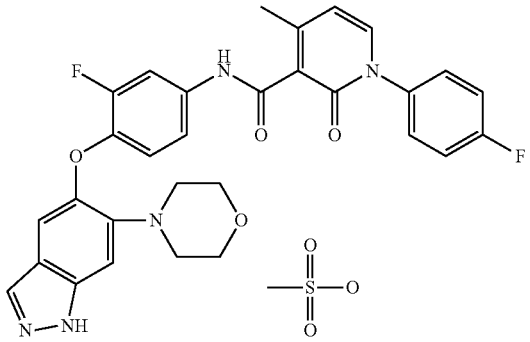 | 558.1 |
| 38 | N-(3-Fluoro-4-(6-(6-methylpyridin-3-yl)-1H-indazol-5-yloxy(phenyl)-1-(4-fluorophenyl)-4,6-dimethyl-2-oxo-1,2-dihydropyridine-3-carboxamide methanesulfonate | 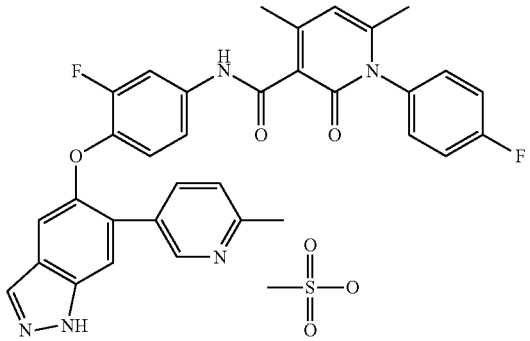 | 578.1 |

-continued

| Ex. No. | Chemical name | Structure | Physical data MS (m/z) (M + H) |
|---|---|---|---|
| 39 | N-(3-Fluoro-4-(6-morpholino-1H-indazol-5-yloxy)phenyl)-2-(4-fluorophenyl)-6-methyl-3-oxo-2,3-dihydropyridazine-4-carboxamide | 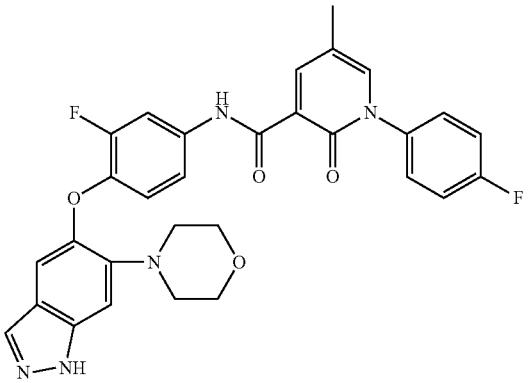 | 559.2 |
| 40 | N-(4-(6-(1,3-Dimethyl-1H-pyrazol-5-yl)-1H-indazol-5-yloxy)-3-fluorophenyl)-2-(4-fluorophenyl)-3-oxo-2,3-dihydropyridazine-4-carboxamide | 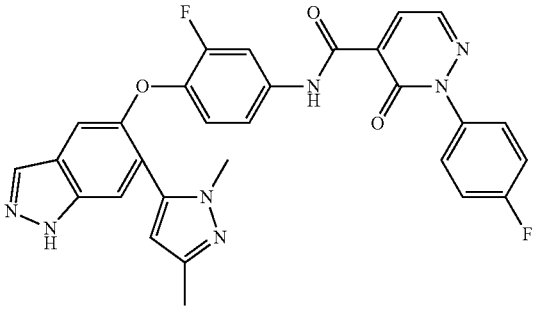 | 554.2 |
| 41 | N-(3-Fluoro-4-(6-(pyridin-4-yl)-1H-inadazol-5-yloxy(phenyl)-1,5-dimethyl-3-oxo-2-phenyl-2,3-dihydro-1H-pyrazole-4-carboxamide methanesulfonate | 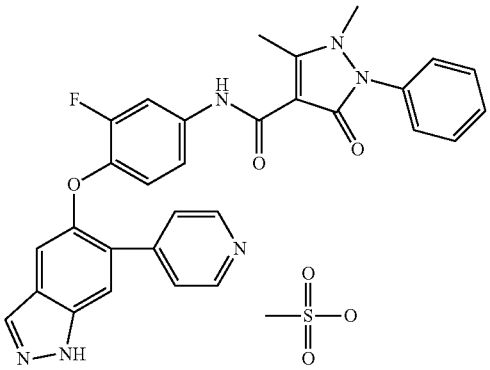 | 535.2 |
| 42 | N-(3-Fluoro-4-(6-morpholino-1H-indazol-5-yloxy)phenyl)-2-(4-fluorophenyl)-2-oxo-2,3-dihydropyridazine-4-carboxamide | 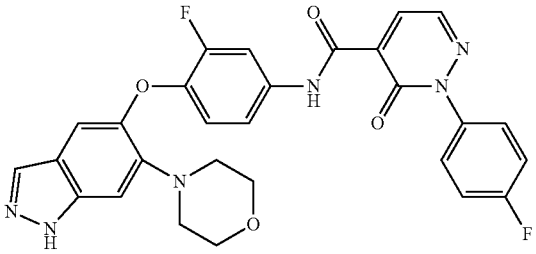 | 545.1 |

-continued

| Ex. No. | Chemical name | Structure | Physical data MS (m/z) (M + H) |
|---|---|---|---|
| 43 | N-(4-(6-(1,3-Dimethyl-1H-pyrazol-5-yl)-1H-indazol-5-yloxy)-3-fluorophenyl)-1-(4-fluorophenyl)-4,6-dimethyl-2-oxo-1,2-dihydropyridine-3-carboxamide methanesulfonate | 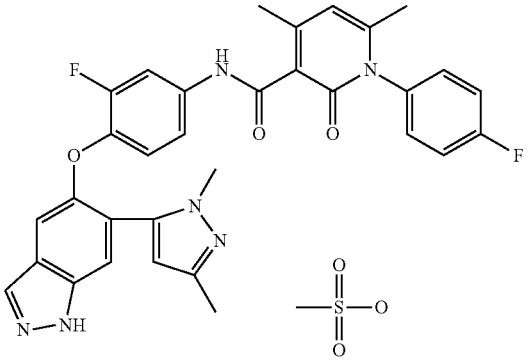 | 581.1 |
| 44 | N-(4-(6-(2,6-Dimethylpyridin-4-yl)-1H-indazol-5-yloxy)-3-fluorophenyl)-2-(4-fluorophenyl)-1,5-dimethyl-3-oxo-2,3-dihydro-1H-pyrazole-4-carboxamide methanesulfonate | 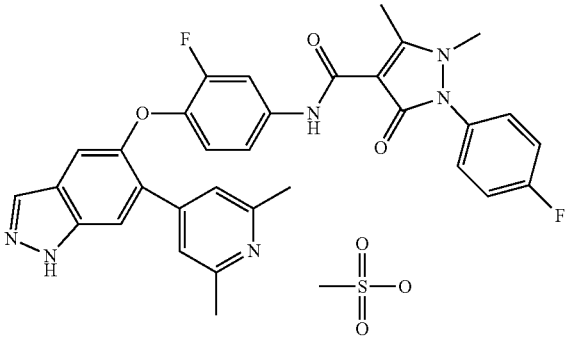 | 581.2 |
| 45 | N-(3-Fluoro-4-(6-(2-methylpyridin-4-yl)-1H-indazol-5-yloxy)phenyl)-2-(4-fluorophenyl)-1-methyl-3-oxo-5-(piperidin-1-ylmethyl)-2,3-dihydro-1H-pyrazole-4-carboxamide | 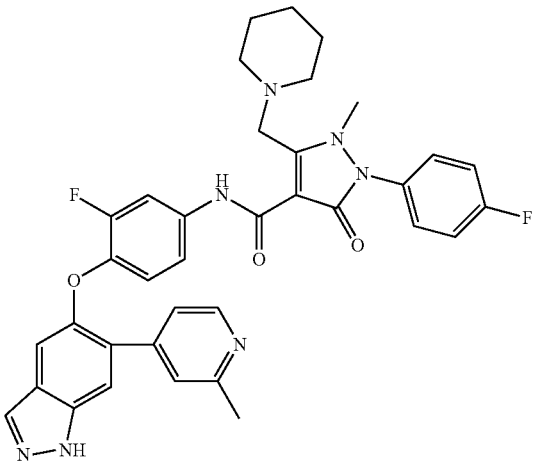 | 650.1 |
| 46 | N-(3-Fluoro-4-(6-(2-methoxypyrimidin-5-yl)-1H-indazol-5-yloxy)phenyl)-1-(4-fluorophenyl)-2-oxo-1,2-dihydropyridine-3-carboxamide | 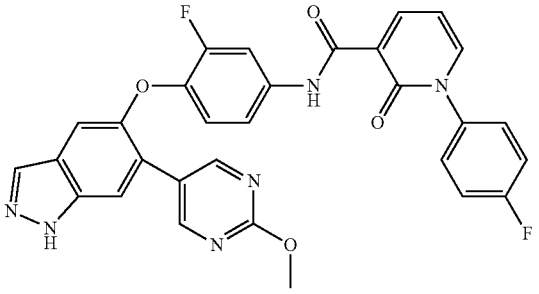 | 567.2 |

-continued

| Ex. No. | Chemical name | Structure | Physical data MS (m/z) (M + H) |
|---|---|---|---|
| 47 | N-(3-Fluoro-4-(6-(2-methylpyridin-4-yl)-1H-indazol-5-yloxy)phenyl)-2-(4-fluorophenyl)-3-oxo-2,3-dihydropyridazine-4-carboxamide | 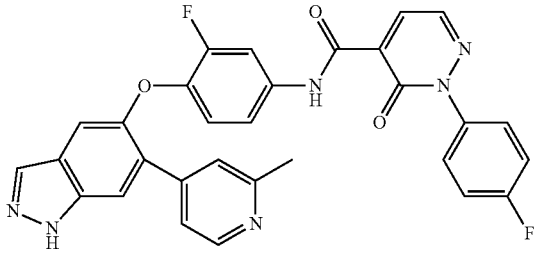 | 551.2 |

Example 48

N-(4-(6-Amino-1-methyl-1H-indazol-5-yloxy)-3-fluorophenyl)-1-(4-fluorophenyl)-6-methyl1-2-oxo-1,2-dihydropyridine-3-carboxamide methanesulfonate

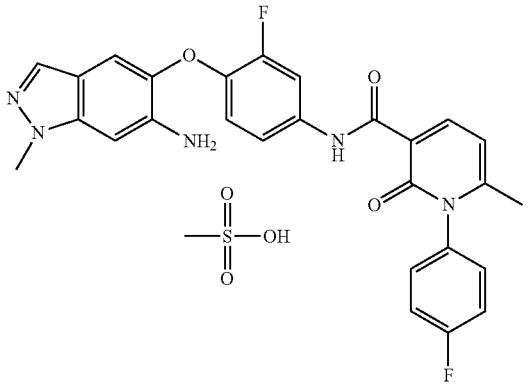

To a 10 mL screw-cap vial is added 5-(4-amino-2-fluorophenoxy)-N-benzhydryl-1-methyl-1H-indazol-6-amine (91 mg, 208 μmol), 1-(4-fluorophenyl)-6-methyl-2-oxo-1,2-dihydropyridine-3-carboxylic acid (66.7 mg, 269.78 μmol), EDCI (90.9 mg, 466.9 μmol) and HOBt (47.7 mg, 311.3 μmol) followed by DMF (2 mL, 25.9 mmol). To the mixture is added DIPEA (90.5 μL, 518.8 μmol) and the mixture is stirred at RT for 12 hours. Additional EDCI (50 mg), HOBt (25 mg), DIPEA (0.02 mL), and 1-(4-fluorophenyl)-6-methyl-2-oxo-1,2-dihydropyridine-3-carboxylic acid (40 mg) are added and the mixture is stirred for an additional 24 hours. The reaction is diluted into EtOAc (100 mL) and washed with saturated aqueous sodium chloride (3×25 mL). The combined aqueous solution is extracted with EtOAc (1×25 mL). The combined organic solution is dried over $Na_2SO_4$, filtered, and concentrated to dryness. The residue is purified on a silica gel column eluting with DCM (A) and a 10% MeOH in DCM solution (B), gradient from 100% (A) to 90%(A): 10%(B) over 60 min to give a clear wax material as the desired product (114 mg, 82% yield). MS (m/z) 667.8 (M+H).

To a 25 mL round bottom flask is added N-(4-(6-(benzhydrylamino)-1-methyl-1H-indazol-5-yloxy)-3-fluorophenyl)-1-(4-fluorophenyl)-6-methyl-2-oxo-1,2-dihydropyridine-3-carboxamide (100 mg, 149.7 μmol) and DCM (15 mL, 15.6 mmol) followed by the addition of triethylsilane (0.3 mL, 1.8 mmol) and TFA (2 mL, 26.9 mmol). The reaction mixture is stirred at RT for 3 hours. The solvent is removed and then the residue is diluted in DCM (50 mL) and washed with a saturated $NaHCO_3$ solution (1×25 mL). The aqueous layer is extracted with DCM (1×25 mL) and the combined organic solution is dried with $Na_2SO_4$, filtered and concentrated. The residue is purified on a silicas gel column eluting wiht DCM (A) and a 10% MeOH in a DCM solution (B), gradient from 100% (A) to 80%(A):20%(B) over 50 min, held at 80:20 ratio for 5 min then gradient to 70%(A):30%(B) over 5 min to give a white solid material as the desired product (67 mg, 90% yield). MS (m/z): 501.8 (M+H).

to a round bottom flask is added N-(4-(6-amino-1-methyl-1H-indazol-5-yloxy)-3-fluorophenyl)-1-(4-fluorophenyl)-6-methyl-2-oxo-1,2-dihydropyridine-3-carboxamide (47.5 mg, 94.7 μmol) in DCM (2 mL, 31.2 mmol) and MeOH (2 mL, 49.4 mmol). $MeSO_3H$ (6.2 μL, 94.7 μmol) in MeOH is added. The solution is concentrated to give a light yellow solid (54 mg, 96% yield). MS (m/z): 501.8 (M+H).

The following compounds are prepared essentially by the method of Example 48:

| Ex. No. | Chemical name | Structure | Physical data MS (m/z) (M + H) |
|---|---|---|---|
| 49 | N-(4-(6-Amino-1-methyl-1H-indazol-5-yloxy)-3-fluorophenyl)- 1-(4-fluorophenyl)-2-oxo-1,2-dihydropyridine-3-carboxamide methanesulfonate | 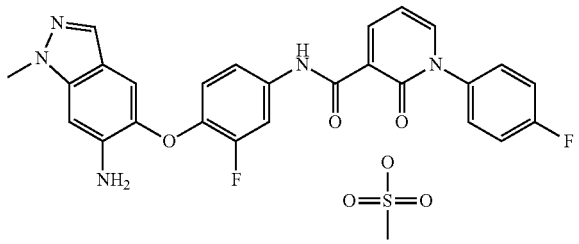 | 487.8 |

Example 50

N-(4-(6-Amino-1H-indazol-5-yloxy)-3-fluorophenyl)-6-methyl-2-oxo-1-phenyl-1,2-dihydropyridine-3-carboxamide methanesulfonate

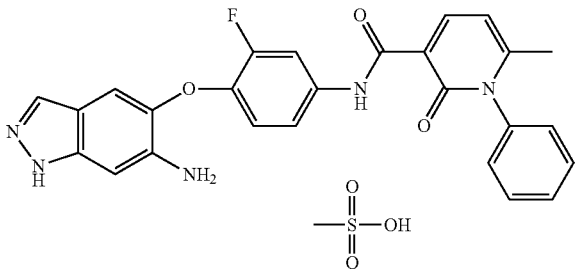

To a solution of tert-butyl 5-(4-amino-2-fluorophenoxy)-1H-indazol-6-ylcarbamate (170 mg, 474 μmol) and 6-methyl-2-oxo-1-phenyl-1,2-dihydropyridine-3-carboxylic acid (120 mg, 0.52 mmol) in DMF (5 mL) is added HOBt (60 mg, 0.44 mmol), EDCI (90 mg, 0.47 mmol) and N-methylmorpholine (0.5 mL). After the reaction mixture is stirred at 60° C. overnight, it is partitioned between EtOAc (50 mL) and saturated aqueous $NH_4Cl$ (30 mL). The organic phase is separated, dried and concentrated, and the residue is purified by silica gel column chromatography eluting with PE:EtOAc (1:1) to give the product (65 mg, 24. 1% yield) MS (m/z): 570.2 [M+H]).

To a solution of tert-butyl 5-(2-fluoro-4-(6-methyl-2-oxo-1-phenyl-1,2-dihydropyridine-3-carboxamido)phenoxy)-1H-indazol-6-ylcarbamate (65 mg, 0.114 mmol) in DCM (10 mL) is added TFA (1 mL, 13.5 mmol). After the reaction is stirred at RT overnight, it is concentrated. The residue is partitioned with saturated aqueous $NaHCO_3$ (30 mL) and DCM (50 mL), and the organic phase is separated, dried and concentrated. The residue is purified by silica gel column chromatography eluting with DCM:MeOH (20:1) to give the product (35 mg, 65.3% yield). MS (m/z): 470.1 (M+H).

To a solution of N-(4-(6-amino-1H-indazol-5-yloxy)-3-fluorophenyl)-6-methyl-2-oxo-1-phenyl-1,2-dihydropyridine-3-carboxamide (35 mg, 74.6 μmol) in acetone (10 mL) is added $MeSO_3H$ (7.16 mg, 74.6 μmol). After the reaction mixture is stirred at RT for 0.5 hour, it is concentrated. The residue is washed with ether and dried to give N-(4-(6-amino-1H-indazol-5-yloxy)-3-fluorophenyl)-6-methyl-2-oxo-1-phenyl-1,2-dihydropyridine-3-carboxamide methanesulfonate (39 mg, 92.5% yield). MS (m/z): 470.1 (M+H). The following compounds are prepared essentially by the method of Example 50:

| Ex. No. | Chemical name | Structure | Physical data MS (m/z) (M + H) |
|---|---|---|---|
| 51 | N-(4-(6-Amino-1H-indazol-5-yloxy)-3-fluorophenyl)-1-(4-fluorophenyl)-2-oxo-1,2-dihydropyridine-3-carboxamide | 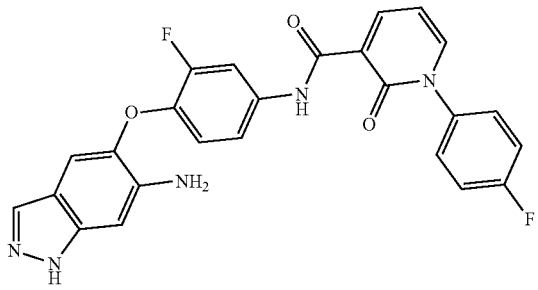 | 474.1 |
| 52 | N-(4-(6-Amino-1H-indazol-5-yloxy)-3-fluorophenyl)-1-(4-fluorophenyl)-4,6-dimethyl-2-oxo-1,2-dihydropyridine-3-carboxamide methanesulfonate | 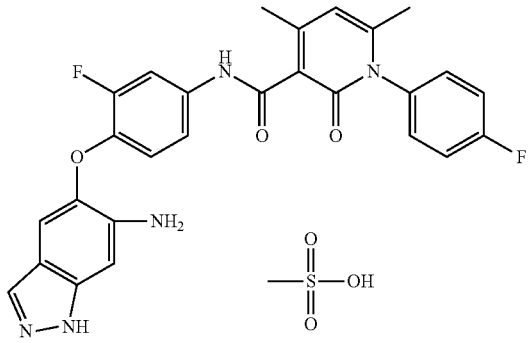 | 502.2 |

-continued

| Ex. No. | Chemical name | Structure | Physical data MS (m/z) (M + H) |
|---|---|---|---|
| 53 | N-(4-(6-Amino-1H-indazol-5-yloxy)-3-fluorophenyl)-1-(4-fluorophenyl)-6-methyl-2-oxo-1,2-dihydropyridine-3-carboxamide | 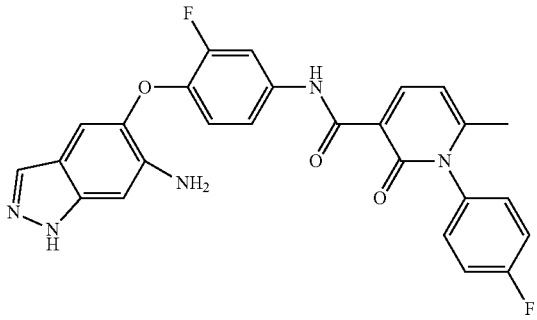 | 488.1 |
| 54 | N-(4-(6-(6-Aminopyridin-3-yl)-1H-indazol-5-yloxy)-3-fluorophenyl)-2-(4-fluorophenyl)-3-oxo-2,3-dihydropyridazine-4-carboxamide | 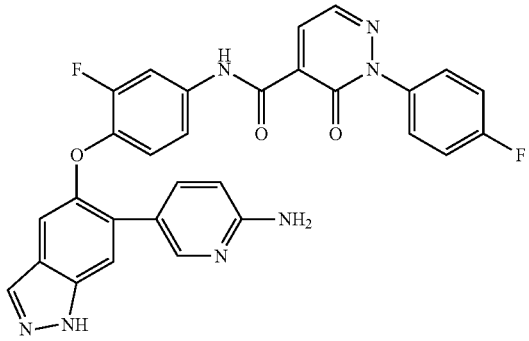 | 552.1 |

Example 55

N-(3-Fluoro-4-(6-(2-methylmorpholino)-1H-indazol-5-yloxy)phenyl)-1-(4-fluorophenyl)-2-oxo-1,2-dihydropyridine-3-carboxamide

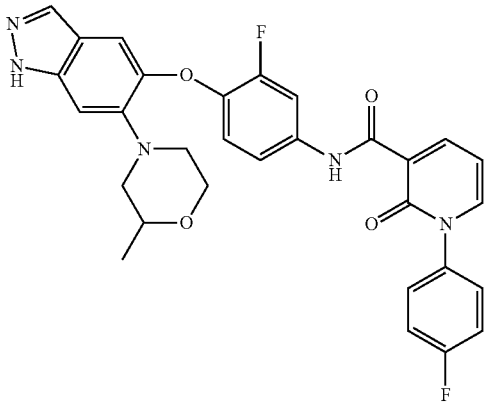

To a 10 mL screw-cap vial is added 3-fluoro-4-(6-(2-methylmorpholino)-2-(tetrahydro-2H-pyran-2-yl)-2H-indazol-5-yloxy)aniline (44 mg, 103.17 μmol), 1-(4-fluorophenyl)-2-oxo-1,2-dihydropyridine-3-carboxylic acid (42 mg, 0.18 mmol), EDCI (45.177 mg, 232.13 μmol), HOBT (23.699 mg, 154.75 μmol) followed by DMF (5 mL, 64.66 mmol) and DIPEA (44.980 μL, 257.92 μmol). The reaction mixture is stirred at RT overnight. The reaction is diluted into EtOAc (50 mL) and washed with saturated aqueous sodium chloride (5×25 mL). Organic layers are dried over $Na_2SO_4$, filtered, and concentrated to dryness. The residue is purified on a silica gel column eluting with hexanes (A) and EtOAc (B), gradient from 80% (A): 20% (B) to 30% (A): 70% (B) over 40 min, hold at 30:70 ratio for 15 min to give a yellow solid as desired product N-(3-fluoro-4-(6-(2-methylmorpholino)-2-(tetrahydro-2H-pyran-2-yl)-2H-indazol-5-yloxy)phenyl)-1-(4-fluorophenyl)-2-oxo-1,2-dihydropyridine-3-carboxamide (70 mg, 99% yield). MS (m/z): 641.8 (M+H).

To a round bottom flask is added N-(3-fluoro-4-(6-(2-methylmorpholino)-2-(tetrahydro-2H-pyran-2-yl)-2H-indazol-5-yloxy)phenyl)-1-(4-fluorophenyl)-2-oxo-1,2-dihydropyridine-3-carboxamide (66 mg, 102.86 μmol) and MeOH (5 mL, 123.54 mmol). To the resulting mixture is added $MeSO_3H$ (20.229 μL, 308.57 μmol) and the reaction mixture is heated to 40° C. for 6 hours. The reaction mixture is concentrated and dissolved in DCM (100 mL). The solution is washed with a mixture of saturated aqueous sodium chloride (20 mL) and saturated aqueous sodium bicarbonate solution (1×20 mL). The organic solution is extracted with DCM (1×25 mL) and dried over $Na_2SO_4$, filtered and concentrated. The residue is purified on a silica gel column eluting with DCM (A) and a 10% MeOH in DCM solution (B), gradient from 100% (A) to 70%(A):30%(B) over 60 min to give a light yellow solid as the desired product (40 mg, 62% yield). MS (m/z): 557.8 (M+H).

The following compounds are prepared essentially by the method of Example 55:

| Ex. No. | Chemical name | Structure | Physical data MS (m/z) (M + H) |
|---|---|---|---|
| 56 | (R)-N-(3-Fluoro-4-(6-(2-methylmorpholino)-1H-indazol-5-yloxy)phenyl)-1-(4-fluorophenyl)-2-oxo-1,2-dihydropyridine-3-carboxamide | 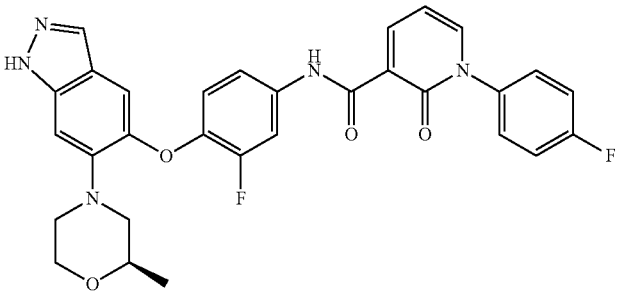 | 558.2 |
| 57 | (R)-N-(3-Fluoro-4-(6-(2-methylmorpholino)-1H-indazol-5-yloxy)phenyl)-1-(4-fluorophenyl)-6-methyl-2-oxo-1,2-dihydropyridine-3-carboxamide | 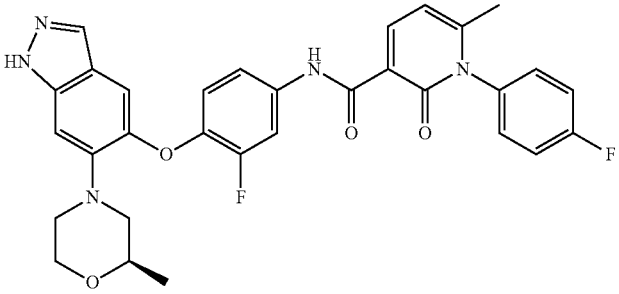 | 572.2 |
| 58 | N-(4-(6-Cyclopropyl-1H-indazol-5-yloxy)-3-fluorophenyl)-1-(4-fluorophenyl)-2-oxo-1,2-dihydropyridine-3-carboxamide | 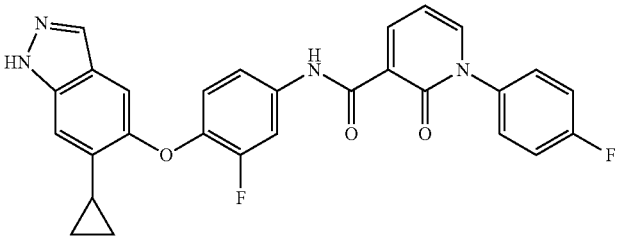 | 499 |
| 59 | N-(4-(6-Cyclopropyl-1H-indazol-5-yloxy)-3-fluorophenyl)-1-(4-fluorophenyl)-6-methyl-2-oxo-1,2-dihydropyridine-3-carboxamide | 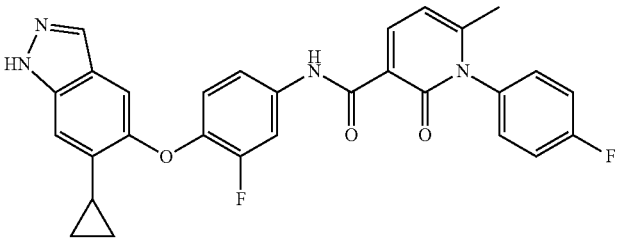 | 512.8 |
| 60 | N-(4-(6-((2S,6R)-2,6-Dimethylmorpholino)-1H-indazol-5-yloxy)-3-fluorophenyl)-1-(4-fluorophenyl)-2-oxo-1,2-dihydropyridine-3-carboxamide | 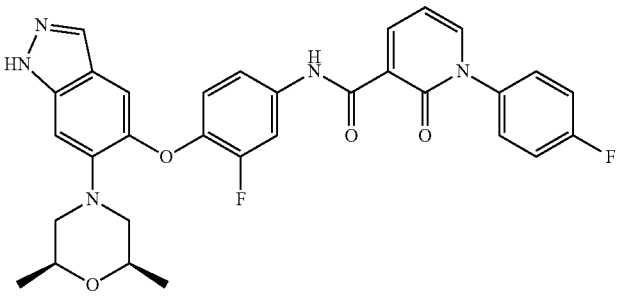 | 572.2 |

-continued

| Ex. No. | Chemical name | Structure | Physical data MS (m/z) (M + H) |
|---|---|---|---|
| 61 | N-(4-(6-(2,2-Dimethylmorpholino)-1H-indazol-5-yloxy)-3-fluorophenyl)-1-(4-fluorophenyl)-2-oxo-1,2-dihydropyridine-3-carboxamide | 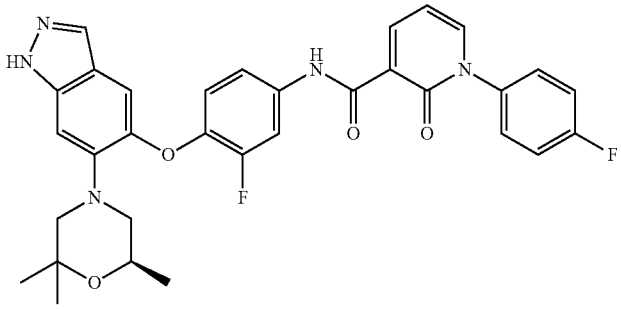 | 572.2 |
| 62 | N-(3-Fluoro-4-(6-morpholino-1H-indazol-5-yloxy(phenyl)-1-(4-fluorophenyl)-4,6-dimethyl-2-oxo-1,2-dihydropyridine-3-carboxamide | 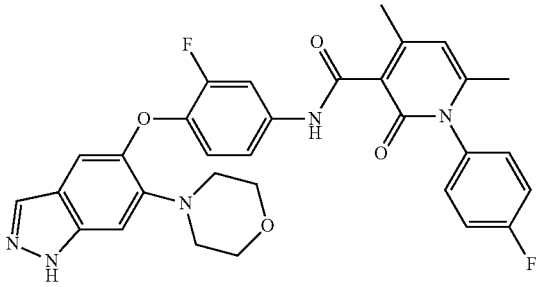 | 571.8 |
| 63 | N-(3-Fluoro-4-(6-(4-(methylsulfonyl)phenyl)-1H-indazol-5-yloxy)phenyl)-1-(4-fluorophenyl)-2-oxo-1,2-dihydropyridine-3-carboxamide | 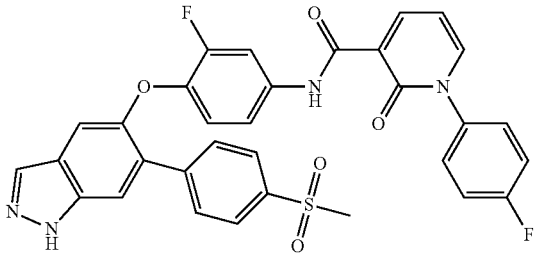 | 613.1 |
| 64* | N-(3-Fluoro-4-(6-fluoro-1H-indazol-5-yloxy(phenyl)-1-(4-fluorophenyl)-6-methyl-2-oxo-1,2-dihydropyridine-3-carboxamide methanesulfonate | 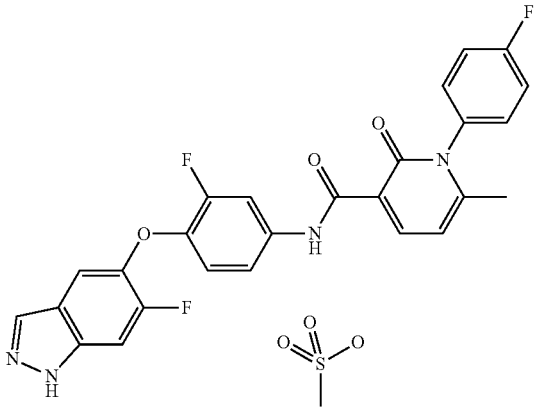 | 491.2 |

-continued

| Ex. No. | Chemical name | Structure | Physical data MS (m/z) (M + H) |
|---|---|---|---|
| 65 | 5-(2-Fluoro-4-(1-(4-fluorophenyl)-6-methyl-2-oxo-1,2-dihydropyridine-3-carboxamido)phenoxy)-N-(tetrahydro-2H-pyran-4-yl)-1H-indazole-6-carboxamide | 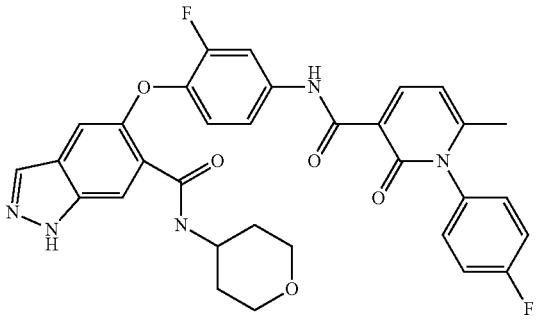 | 600.2 |

*Methanesulfonate salt is prepared essentially by the same method of salt formation step in Example 3.

The following assays demonstrate that certain compounds of the present invention potently inhibit c-Met phosphorylation in cells, potently inhibit c-Met in vivo, and demonstrate dose dependent anti-tumor activity in certain xenograft models.

c-Met Protein Expression and Purification

The kinase domain (KD) of human c-Met (from Gly 966 to Ser 1390, NCBI NM_000245) is cloned into a pFastBac® RHT vector (Invitrogen, Carlsbad, Calif.). The His-c-Met KD construct is transposed into Baculovirus DNA using a Bac-to-Bac® system (Invitrogen). SF9 cells are infected with the recombinant baculovirus. The infected cells are harvested by centrifugation and the cell pellet is collected and stored at −80° C. Cells are lysed in buffer A (40 mM tris(hydroxymethyl)aminomethane (Tris), pH 7.5, 500 mM NaCl, 20% glycerol, and 10 mM imidazole). Cell lysates are homogenized and centrifuged. Supernatants are incubated with nickel-nitrilotriacetic (Ni—NTA) resin and loaded onto a column. Proteins are eluted with buffer B (buffer A plus 0.3 M imidazole) and c-Met containing fractions are pooled together, loaded onto a Superdex®200 column (Amershan Bioscience, Piscataway, N.J.), eluted with buffer C (40 mM Tris, pH 7.5, 250 mM NaCl, and 10% glycerol).

HGF Stimulated Met (pY1349) NCI-H460 Cell-based ELISA

NCI-H460 cells (purchased from ATCC) are cultured in RPMI 1640 media (Invitrogen) supplemented with 10% Fetal Bovine Serum (FBS) and plated (prior to becoming 70% confluent) in 96-well flat-bottom plates at a density of 20,000 cells per well in 80 μL volume. The cells are then incubated overnight in a cell culture incubator (5% $CO_2$, 95% Relative Humidity (RH) and 37° C.) and allowed to attach to the plate. The following morning the cells are washed with 2 volumes of a Reduced Serum Media (RSM) (RPMI 1640 media supplemented with 0.5% FBS). After removal of the last wash, 80 μL of RSM is added to each well of the cell plates. The cell plates are incubated for 2.5 hours in a cell culture incubator, and then dosed with compounds. Compound inhibitors are first solubilized at 10 mM in 100% DMSO and then diluted to 100 μM with 2% DMSO RSM. Subsequently compound serial dilutions (1:3) are prepared over a 100 μM to 0.005 μM range. Cells are dosed with the addition of 20 μL of compound stock to produce a final DMSO concentration of 0.4% and a final compound concentration dose range between 20 and 0.001 μM. After dosing with compounds the cells plates are gently agitated to mix and then allowed to incubate for 30 min in a cell culture incubator. After dose completion, the cells are stimulated with the addition of 20 μL per well of Hepatocyte Growth Factor (HGF) at a final concentration of 100 ng/mL in RSM (all wells except MIN wells are stimulated, MIN wells are dosed with 20 μL RSM). After 10 min incubation in a cell culture incubator, the liquid is removed from the cell plate wells, and the cells are lysed by the addition of 50 μL of ice-cold Meso Scale Discovery® (MSD, Gaithersburg, Md.) 1× Lysis Buffer (150 mM NaCl, 20 mM Tris, pH 7.5, 1 mM EDTA, 1 mM ethylene glycol tetraacetic acid, and 1% TRITON® X-100) supplemented with Phosphatase I and II and Protease inhibitors (Sigma, St. Louis, Mo.). After lysis at RT for 30 min the lysates are transferred to and captured on a MSD® Multi-Spot 96-well 4-spot PhosphoMet plate that is BSA-blocked (at 30 mg/mL Block A in 1× Tris Wash Buffer) and then washed one time with Tris Wash Buffer. After 2 hours capture (at RT) the lysates are removed from the MSD® plate and the plate is washed with 1X Tris Wash Buffer. After blotting, 25 μL of 5 nM Sulfo-Tag Anti-Total Met antibody (detection antibody, MSD® prepared in 1× Tris Wash Buffer supplemented with 10 mg/mL BSA and 0.1% Blocker D-R (MSD®)) is added to the wells of the MSD® plate. After 1 hour capture (at RT) the MSD® plate wells are washed with 1× Tris Wash Buffer, and then 150 μL of 1× Read Buffer T (with surfactant, MSD®) is added. Immediately after the addition of the Read Buffer, the plates are analyzed with a SECTOR 6000 MSD® Imager plate reader. Relative $IC_{50}$ values are determined using MSD activity units by calculating percent inhibition with respect to on-plate "MIN" and "MAX" controls and then fitting the percent inhibition values and ten-point dose response data to a four-parameter logistic equation. This assay has a Minimum Significant Ratio (MSR) of 2.06. For all exemplified compounds the $IC_{50}$ values are less than 0.2 μM. For example, the average (n=6) $IC_{50}$ value (50% inhibitory concentration ) of Example 1 in this assay is 0.0352 μM, indicating it potently inhibits c-Met phosphorylation in cells.

c-Met In Vivo Target Inhibition Assay

S114 cells (licensed from PHS, over-express both human HGF and human c-Met) are cultured in a growth media (Dulbecco's Modified Eagle Medium) supplemented with 10% fetal calf serum and expanded. Cells are harvested and washed twice with phosphate buffered saline and $2\times10^6$ cells are mixed with equal volume of BD Matrigel™ matrix (BD Bioscience, Franklin, N.J.), and injected subcutaneously into the flank of nude mice (athymic nude, from Harlan, Indianapolis, Ind.). At day 8 after implant, compounds (formulated in 10% acacia or 1% carboxymethylcellulose/0.5% sodium lauryl sulfate/0.05% antifoam as suspension) are administered to animals by oral gavage at 50 mg/kg. Animals are sacrificed at 2 hours post dose, and tumors are harvested and stored frozen until needed.

Frozen tumors are pulverized using motar-pastel. The pulverized tissues are transferred to a tube containing Lysing Matrix D beads (MP Biomedicals, Solon, Ohio) and 600 μL lysis buffer (RIPA buffer, containing 50 mM Tris-HCl, pH 7.4, 150 mM NaCl, 1% NP-40, 0.5% sodium deoxycholate, 0.1% SDS, from Boston Bioproducts). A FastPrep® Cell Disrupter (MP Biomedicals) is used to disrupt the tissue and lyse the cells. Lysates are passed through a 20 gauge needle and transferred to a clean tube. Protein concentration is determined by Bradford method.

Tumor lysates are loaded onto MSD® phosphor-Met ELISA plates and phosphor-c-Met level is determined using the same protocol as H460 cell-based ELISA. For all exemplified compounds the S114 in vivo inhibition values are equal or greater than 50% at the dose of 50 mg/kg. For example, Example 1 is a potent inhibitor of c-Met phosphorylation with an $ED_{50}$ value (dose that produces 50% inhibition in tumor of 2.9 mg/kg, indicating it is a potent c-Met inhibitor in vivo.

Xenograft Tumor Models

Human glioblastoma cells U87MG, human gastric cancer cells MKN45, human non small cell lung cancer cells H441, and human renal carcinoma cells Caki-1 are expanded in culture, harvested, and injected subcutaneously onto the rear flank of athymic nude mice. Testing compound is prepared in an appropriate vehicle and is administered by oral gavage when tumors are established (7-21 days after implant). Tumor response is determined by tumor volume measurement performed twice a week during the course of treatment. Tumor volume inhibition (% growth inhibition) is calculated by comparing treated groups to a vehicle control group. Body weight is taken as a general measurement of toxicity. The Compound of Example 1 demonstrates excellent dose dependent anti-tumor activity in these models. For example, when dosed at 1.3 mg/kg (oral (PO), bi-daily (BID)×35), Example 1 is able to cause 59% growth inhibition of U87MG tumors. At 4 mg/kg dose (PO, BID×35), 82% growth inhibition is achieved. At 12 mg/kg dose (PO, BID×3 5), 92% growth inhibition reaches.

c-Met Relevant Tumors and Xenograft Models c-Met overexpression is a common feature for many human tumors, including lung, breast, colorectal, gastric, renal, pancreatic, head and neck (1,2). c-Met activating mutations in the kinase domain are implicated as the cause for several tumors, such as hereditary papillary renal cell carcinoma, childhood hepatocellular carcinoma, and gastric cancer (3-7). c-Met inhibitors from Pfizer demonstrated antitumor efficacy in many human xenograft tumors, including U87MG, GTL16, H441, Caki-1, and PC3 (8).

1. Christinsen, J G., Burrows, J., and Salgia, R. Cancer Letters 225:1-26, 2005.
2. Birchmeier, C., Birchmeier, W., Gherardi, E., and Vande Woude, GF. Nat Rev Mol Cell Biol 4: 915-925, 2003.
3. Di Renzo, M F., Olivero, M., Martone, T. Et al. Oncogene 19:1547-1555, 2000.
4. Lee, J H., Han, SU, Cho, H. et al. Oncogene 19: 4947-4953, 2000.
5. Ma, P C., Kijima, T., Maulik, G. et al. Cancer Res 63: 6272-6281, 2003.
6. Park, W S., Dong, S M., Kim, S Y. et al. Cancer Res 59: 307-310, 1999.
7. Schmidt, L., Duh, F M., Chen, F., et al. Nat Genet 16: 68-73, 1997.
8. Zou, H Y., Li, Qiuhua., Lee, J H., et al. Cancer Res 67: 4408-4417, 2007.

The compounds of the present invention are preferably formulated as pharmaceutical compositions administered by a variety of routes. Most preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al., eds., 19th ed., Mack Publishing Co., 1995).

The compounds of Formula I are generally effective over a wide dosage range. For example, dosages per day normally fall within the range of about 1 mg to about 200 mg total daily dose, preferably 1 mg to 150 mg total daily dose, more preferably 1 mg to 50 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of the formula:

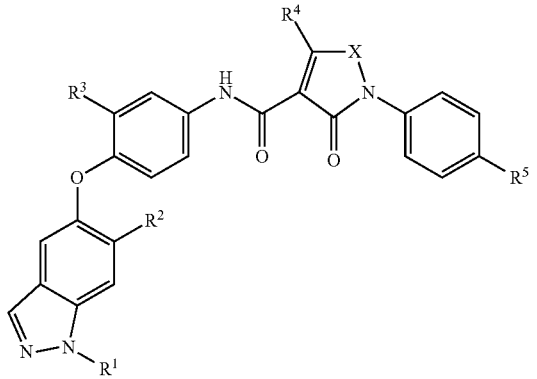

wherein:

$R^1$ is H or methyl;

$R^2$ is amino, dimethylamino, fluoro, cyclopropyl, pyridyl optionally substituted with an amino substituent or 1-2 methyl substituents, pyrazolyl optionally substituted with two methyl substituents, 2-methoxy-pyrimidin-5-yl, 4-methylsulfonylphenyl, tetrahydro-2H-pyran-4-ylamino, (tetrahydro-2H-pyran-4-yl)amino carbonyl, or a morpholin-4-yl substituent:

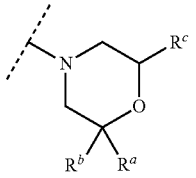

where $R^a$, $R^b$ and $R^c$ are independently selected from H or methyl;

$R^3$ is H or F;

$R^4$ is H, methyl, piperidin-1-ylmethyl, morpholin-4-ylmethyl, or pyrazol-1-ylmethyl;

$R^5$ is H or F; and

X is CH═N, CH═CH, CH═C($CH_3$), C($CH_3$)═CH, C($CH_3$)═N, N($CH_3$), or [C(morpholin-4ylmethyl)═CH] *C(morpholin-4-ylmethyl)═CH*;

or a pharmaceutically acceptable salt thereof.

2. The compound according to claim 1, or a pharmaceutically acceptable salt thereof, wherein $R^2$ is amino, dimethylamino, cyclopropyl, pyridyl optionally substituted with an amino substituent or 1-2 methyl substituents, pyrazol-4-yl, or a morpholin-4-yl.

3. The compound according to claim 1, or a pharmaceutically acceptable salt thereof, wherein $R^2$ is amino, dimethylamino, pyrazol-4-yl, or a morpholin-4-yl.

4. The compound according to claim 1, or a pharmaceutically acceptable salt thereof, wherein $R^2$ is pyrazol-4-yl.

5. The compound according to claim 1, or a pharmaceutically acceptable salt thereof, wherein $R^4$ is H, methyl, or morpholin-4-ylmethyl.

6. The compound according to claim 1, or a pharmaceutically acceptable salt thereof, wherein $R^4$ is H.

7. The compound according to claim 1, or a pharmaceutically acceptable salt thereof, wherein X is CH═CH or CH═C($CH_3$).

8. [The compound according to claim 1 which is ] N-(3-fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or a pharmaceutically acceptable salt thereof.

9. The compound according to claim 1 which is N-(3-fluoro-4-(1-methyl-6-(1H-pyrazol-4-yl)-1H-indazol-5-yloxy)phenyl)-6-methyl-2-oxo-1-phenyl-1,2-dihydropyridine-3-carboxamide or a pharmaceutically acceptable salt thereof.

10. The compound according to claim 1 wherein the pharmaceutically acceptable salt is a methanesulfonate salt.

11. The compound according to claim 1 wherein the particle size is less than 10 microns.

12. A pharmaceutical composition comprising a compound of [claim 1 or a pharmaceutically acceptable salt thereof] *the formula:*

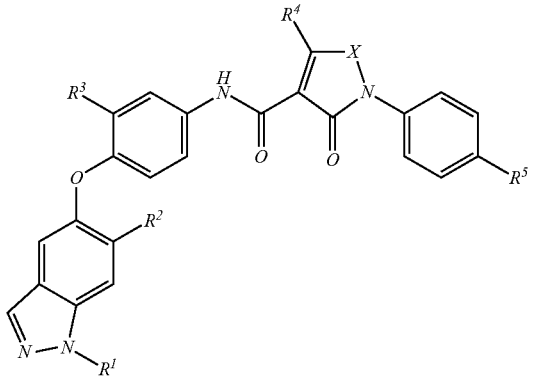

*wherein:*

*$R^1$ is H or methyl;*

*$R^2$ is amino, dimethylamino, fluoro, cyclopropyl, pyridyl optionally substituted with an amino substituent or 1-2 methyl substituents, pyrazolyl optionally substituted with two methyl substituents, 2-methoxy-pyrimidin-5-yl, 4-methylsulfonylphenyl, tetrahydro-2H-pyran-4-ylamino, (tetrahydro-2H-pyran-4-yl)amino carbonyl, or a morpholin-4-yl substituent;*

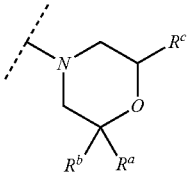

*where $R^a$, $R^b$ and $R^c$ are independently selected from H or methyl;*

*$R^3$ is H or F;*

*$R^4$ is H, methyl, piperidin-1-ylmethyl, morpholin-4-ylmethyl, or pyrazol-1-ylmethyl;*

*$R^5$ is H or F; and*

*X is CH═N, CH═CH, CH═C($CH_3$), C($CH_3$)═CH, C($CH_3$)═N, N($CH_3$), or C(morpholin-4-ylmethyl)═CH;*

*or a pharmaceutically acceptable salt thereof*, and a pharmaceutically acceptable carrier, diluent or excipient.

13. A method of treating cancer selected from the group consisting of lung cancer, breast cancer, colorectal cancer, renal cancer, pancreatic cancer, head cancer, neck cancer, hereditary papillary renal cell carcinoma, childhood hepatocellular carcinoma, and gastric cancer in a mammal comprising administering to a mammal in need of such treatment an effective amount of a compound of [claim 1 or a pharmaceutically acceptable salt thereof] *the formula:*

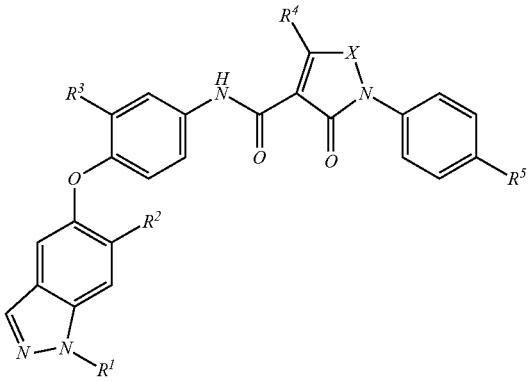

*wherein:*

*$R^1$ is H or methyl;*

*$R^2$ is amino, dimethylamino, fluoro, cyclopropyl, pyridyl optionally substituted with an amino substituent or 1-2 methyl substituents, pyrazolyl optionally substituted with two methyl substituents, 2-methoxy-pyrimidin-5-yl, 4-methylsulfonylphenyl, tetrahydro-2H-pyran-4-ylamino, (tetrahydro-2H-pyran-4-yl)amino carbonyl, or a morpholin-4-yl substituent;*

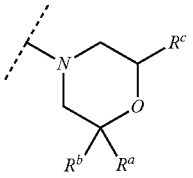

*where $R^a$, $R^b$ and $R^c$ are independently selected from H or methyl;*

*$R^3$ is H or F;*

*$R^4$ is H, methyl, piperidin-1-ylmethyl, morpholin-4-ylmethyl, or pyrazol-1-ylmethyl;*

*$R^5$ is H or F; and*

*X is CH═N, CH═CH, CH═C($CH_3$), C($CH_3$)═CH, C($CH_3$)═N, N($CH_3$), or C(morpholin-4-ylmethyl)═CH;*

*or a pharmaceutically acceptable salt thereof.*

*14. The pharmaceutical composition according to claim 12 wherein the compound is N-(3-fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or a pharmaceutically acceptable salt thereof.*

*15. The method according to claim 13 wherein the compound is N-(3-fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or a pharmaceutically acceptable salt thereof.*

* * * * *